United States Patent
Shapira et al.

(10) Patent No.: US 8,969,831 B2
(45) Date of Patent: Mar. 3, 2015

(54) EXCITATION ENHANCEMENT AND EXTRACTION ENHANCEMENT WITH PHOTONIC CRYSTALS

(71) Applicant: Massachusetts Institute of Technology, Cambridge, MA (US)

(72) Inventors: Ofer Shapira, Cambridge, MA (US); Marin Soljacic, Belmont, MA (US); Bo Zhen, Cambridge, MA (US); Song-Liang Chua, Cambridge, MA (US); Jeongwon Lee, Boston, MA (US); John Joannopoulos, Belmont, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 48 days.

(21) Appl. No.: 13/768,725

(22) Filed: Feb. 15, 2013

(65) Prior Publication Data

US 2014/0230884 A1  Aug. 21, 2014

(51) Int. Cl.
| | |
|---|---|
| G01N 21/64 | (2006.01) |
| H01L 31/055 | (2014.01) |
| H01S 3/16 | (2006.01) |
| G02B 6/122 | (2006.01) |
| G01N 21/65 | (2006.01) |
| H01L 31/054 | (2014.01) |
| B82Y 20/00 | (2011.01) |
| H01S 3/094 | (2006.01) |
| H01S 3/02 | (2006.01) |

(52) U.S. Cl.
CPC .............. *H01L 31/055* (2013.01); *B82Y 20/00* (2013.01); *Y10S 977/759* (2013.01); *Y10S 977/774* (2013.01); *H01S 3/094034* (2013.01); *H01S 3/168* (2013.01); *H01S 3/022* (2013.01); *G02B 6/1225* (2013.01); *G01N 21/658* (2013.01); *G01N 21/648* (2013.01); *H01L 31/054* (2014.12)
USPC .................... 250/458.1; 250/459.1; 977/759; 977/774

(58) Field of Classification Search
USPC ........................................... 250/458.1, 459.1
See application file for complete search history.

(56) References Cited

PUBLICATIONS

C. T. Chan et al., "Dirac cone and double zero materials," AIP Conf. Proc. 1398, 21 (2011); doi 10.1063/1.3644199.
Charles J Choi et al., "Surface-enhanced Raman nanodomes," Nanotechnology 21 415301 (Sep. 13, 2010) doi:10.1088/0957-4484/21/41/415301.

(Continued)

*Primary Examiner* — Mark R Gaworecki
(74) *Attorney, Agent, or Firm* — Cooley LLP

(57) ABSTRACT

Disclosed herein is a system for stimulating emission from at least one an emitter, such as a quantum dot or organic molecule, on the surface of a photonic crystal comprising a patterned dielectric substrate. Embodiments of this system include a laser or other source that illuminates the emitter and the photonic crystal, which is characterized by an energy band structure exhibiting a Fano resonance, from a first angle so as to stimulate the emission from the emitter at a second angle. The coupling between the photonic crystal and the emitter may result in spectral and angular enhancement of the emission through excitation and extraction enhancement. These enhancement mechanisms also reduce the emitter's lasing threshold. For instance, these enhancement mechanisms enable lasing of a 100 nm thick layer of diluted organic molecules solution with reduced threshold intensity. This reduction in lasing threshold enables more efficient organic light emitting devices and more sensitive molecular sensing.

19 Claims, 22 Drawing Sheets

(56) References Cited

PUBLICATIONS

H. Altug et al., "Experimental demonstration of the slow group velocity of light in two-dimensional coupled photonic crystal microcavity arrays," Applied Letters Physics, vol. 86, pp. 111102-1-111102-3 (2005).

J. Bravo-Abad, J. D. Joannopoulos, and M. Soljacic, "Enabling single-mode behavior over large areas with photonic Dirac cones," Proceedings of the National Academy of Sciences of the United States of America, vol. 109, Issue 25, pp. 9761-9765, DOI: 10.1073/pnas.1207335109 (Jun. 19, 2012).

J. Bravo-Abad, J. D. Joannopoulos, M. Soljacic, "Enabling single-mode behavior over large areas with photonic Dirac cones," arXiv:1204.0500 [cond-mat.mes-hall] (Submitted on Apr. 2, 2012).

J. Lee et al., "Observation and Differentiation of Unique High-Q Optical Resonances Near Zero Wave Vector in Macroscopic Photonic Crystal Slabs," Phys. Rev. Lett. 109, 067401 (2012) [5 pages].

K. Sakoda, "Dirac cone in two- and three-dimensional metamaterials," Optics Express, vol. 20, No. 4, pp. 3898-3917 (Feb. 13, 2012; published on-line Feb. 1, 2012).

K. Sakoda, "Double Dirac cones in triangular-lattice metamaterials," Optics Express, vol. 20, No. 9, pp. 9925-9939 (Apr. 23, 2012).

K. Sakoda, "Universality of mode symmetries in creating photonic Dirac cones," J. Opt. Soc. Am. B., vol. 29, No. 10, pp. 2770-2778 (Oct. 2012).

Kent D. Choquette, Dominic F. Siriani, Ansas M. Kasten, et al., "Single Mode Photonic Crystal Vertical Cavity Surface Emitting Lasers," Advances in Optical Technologies, vol. 2012, Article ID 280920, 8 pages, 2012. doi:10.1155/2012/280920.

M. Ibanescu et al., "Ultra-flat bands in two-dimensional photonic crystals," Proc. of SPIE, vol. 6128, 6 pp. (2006).

M. Imada et al., "Coherent two-dimensional lasing action in surface-emitting laser with triangular-lattice photonic crystal structure," Appl. Phys. Lett. 75, 316 (1999); doi: 10.1063/1.124361.

M. Imada, A. Chutinan, S. Noda, and M. Mochizuki, "Multidirectionally distributed feedback photonic crystal lasers," Phys. Rev. B, vol. 65, p. 195306, 2002.

M. Soljacic et al., "Enhancement of nonlinear effects using photonic crystals," Nature Materials, vol. 3, pp. 211-219 (Apr. 2004).

M. Soljacic et al., "Photonic-crystal slow-light enhancement of nonlinear phase sensitivity," J. Opt. Soc. Am. B., vol. 19, No. 9, pp. 2052-2059 (Sep. 2002).

Ofer Shapira, "Nanophotonic structures for enhanced light-matter interaction," presentation at George Washington University on Feb. 16, 2012.

R. A. Sepkhanov, Ya. B. Bazaliy, and C. W. J. Beenakker, "Extremal transmission at the Dirac point of a photonic band structure," Phys. Rev. A 75, 063813 (2007).

S. Fan and J. D. Joannopoulos, "Analysis of guided resonances in photonic crystal slabs," Phys. Rev. B, 65, 235112 (2002).

S. Longhi et al., "X-shaped waves in photonic crystals," Physical Review, vol. 70, pp. 235123-1-235123-7 (2004).

S.-L. Chua et al., "Larger-area single-mode photonic crystal surface-emitting lasers enabled by the accidental Dirac-point," in 2012 IEEE Photonic Conference Proceedings, pp. 346-347, Sep. 23-27, 2012.

W. Kunishi et al., "High-power single-lobed surface-emitting photonic-crystal laser," CLEO/QELS 2006 Conf. Proceedings, pp. 1-2, May 21-26, 2006, doi: 10.1109/CLEO.2006.4627795.

X. Huang et al., "Dirac cones induced by accidental degeneracy in photonic crystals and zero-refractive-index materials," Nature Materials, vol. 10, pp. 582-586 (Aug. 2011).

EXCITATION ENHANCEMENT AND EXTRACTION ENHANCEMENT WITH PHOTONIC CRYSTALS

GOVERNMENT SUPPORT

This invention was made with government support under Contract Nos. DE-SC0001299 and DE-FG02-09ER46577 awarded by the Department of Energy, under Contract No. W911NF-07-D-0004 awarded by the Army Research Office and under Grant No. DMR0819762 awarded by the National Science Foundation. The government has certain rights in the invention.

BACKGROUND

Organic molecules are pervasive in daily life: from natural proteins, to human synthesized fluorescing labels, to organic semiconductors. The interaction of light with such molecules is at the heart of important technological advances in biomolecular detection, fluorescent microscopy, and organic light emitting devices as well as more fundamental studies of cavity quantum electrodynamics and various types of enhanced spectroscopy and sensing. This interaction can be altered or enhanced by placing the organic molecules in a nanostructured cavity where both the lifetime of the resonances and the optical density of states (DOS) can be tailored.

However, there are inherent challenges in incorporating organic molecules in such cavities: first, their dissimilar compositional structure makes it difficult to incorporate them within the high dielectric regions of the cavity where long-lifetime resonances concentrate their electromagnetic energy. Second, micro- and nanostructured cavities typically only have a small portion of their model volumes extending outside their high-dielectric regions, making it challenging to bring external entities precisely to within that volume. Third, it is difficult to pattern organic materials at the nano-scale; indeed, organic patterning processes tend to be incompatible with inorganic processes. These challenges limit experimental realizations of systems of excitons of organic molecules and optical resonances compared to systems of inorganic quantum nano structures.

SUMMARY

Embodiments of the present invention include a system and corresponding method for stimulating emission from at least one emitter, such as an organic molecule, a quantum dot, an organic quantum dot, a quantum well, or an exciton-hole pair. This system may include a photonic crystal and a radiation source. The photonic crystal, which is characterized by an energy band structure exhibiting a Fano resonance, includes a patterned dielectric substrate free of defects and defines a surface to support the source. The radiation source irradiates the source at a first angle with respect to the surface of the photonic crystal so as to cause the source to emit radiation at a second angle with respect to the surface of the photonic crystal. In some examples, the first angle is selected so as to cause the source to emit substantially all of the radiation at the second angle with respect to the photonic crystal's surface.

In at least one embodiment, the photonic crystal has a quality factor of about 10 to about $10^{10}$. This quality factor may extend over about $10^2$ unit cells of the photonic crystal to about $10^{10}$ unit cells of the photonic crystal. The photonic crystal's patterned dielectric substrate defines a plurality of cylindrical holes arrayed on a square lattice.

Embodiments may also include a detector, in optical communication with the one source, to sense the power emitted at the second angle by the source. This detector may be configured to detect fluorescence, phosphorescence, and/or a Raman signal emitted by the source.

In certain embodiments, the detector may be configured to detect an enhanced Raman signal emitted by the source. In these embodiments, the source comprises at least one organic molecule characterized by a Raman resonance frequency, which is substantially equal to the resonance frequency of the Fano resonance. The radiation source excites the organic molecule with coherent radiation at the Fano resonance frequency so as to cause the radiation emitted by the organic molecule to be enhanced via resonant absorption of the coherent radiation by the photonic crystal. The detector, which may include a spectrometer, senses at least one characteristic of this enhanced radiation. For instance, the detector may determine the enhanced radiation's spectrum, which can be used to identify the source.

In some cases, the system also includes a channel and a reservoir in fluid communication with the surface of the photonic crystal. The reservoir stores organic molecules or other sources in solution. This solution flows through the channel the photonic crystal's surface, where it is irradiated and its emission (fluorescence, phosphorescence, or Raman signal) is detected.

Embodiments of the present invention also include a solar concentrator that comprises a photonic crystal and solar cell. The photonic crystal, which is characterized by an energy band structure exhibiting a Fano resonance, absorbs radiation incident over a first solid angle on a first surface of the photonic crystal and emit radiation over a second solid angle that is smaller than the first solid angle via a second surface of the photonic crystal. The solar cell, which is in optical communication with the photonic crystal's second surface, receives at least a portion of the radiation emitted by the photonic crystal via the photonic crystal's second surface. In some embodiments, the photonic crystal comprises at least one layer of dielectric material having a plurality of cylindrical holes arrayed on a square lattice. The solar concentrator may also include a frequency converter, in optical communication with the photonic crystal, that shifts a frequency of the incident radiation to an absorption band of the photonic crystal.

All combinations of the foregoing concepts and additional concepts discussed in greater detail below (provided such concepts are not mutually inconsistent) are part of the inventive subject matter disclosed herein. In particular, all combinations of claimed subject matter appearing at the end of this disclosure are part of the inventive subject matter disclosed herein. Terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1A:
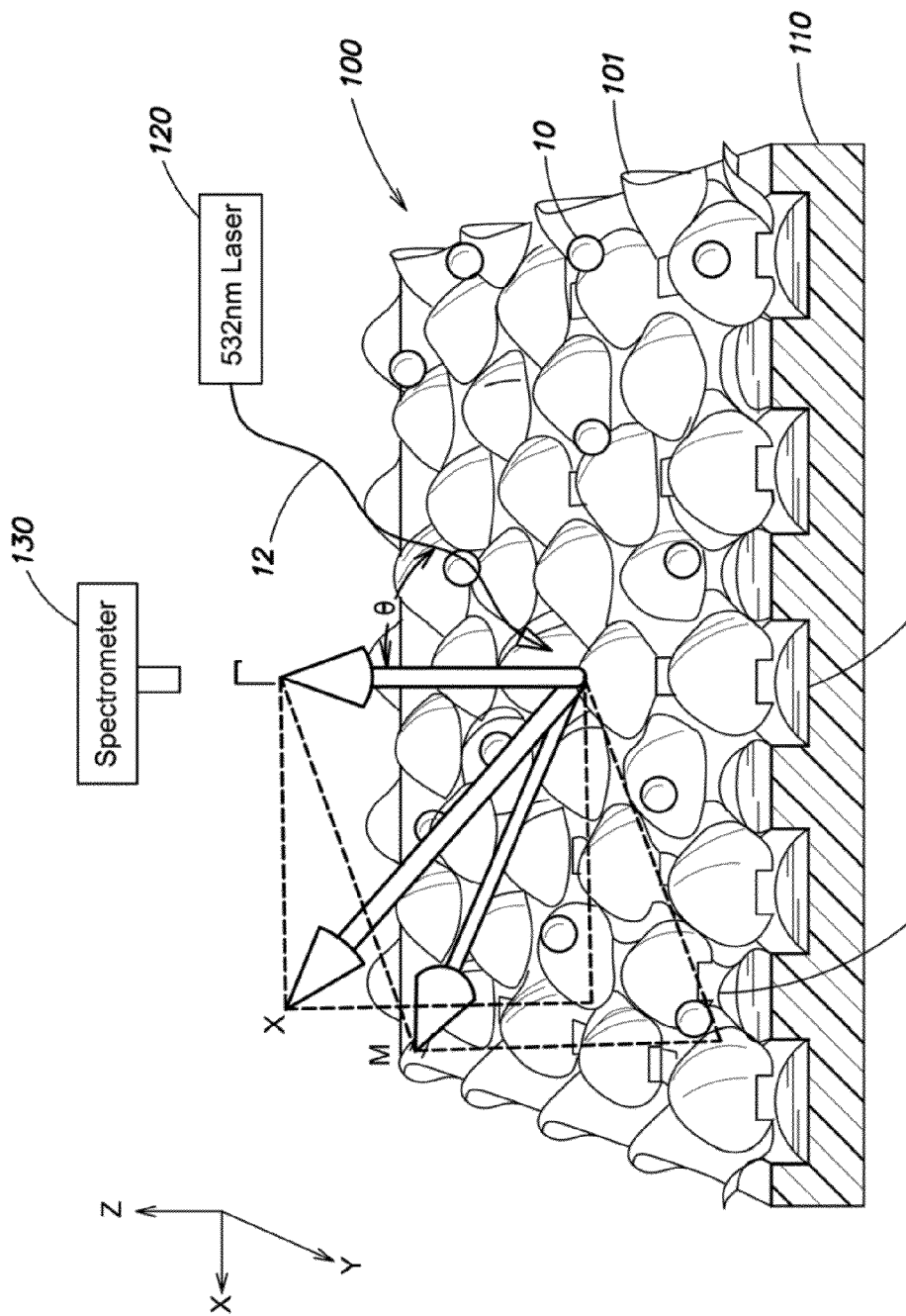
FIG. 1A is a schematic diagram of a photonic crystal with an energy band structure that exhibits a Fano resonance.

Following below are more detailed descriptions of various concepts related to, and embodiments of, inventive systems, methods, and apparatus for enhancing emissions from sources such as organic molecules, quantum dots, quantum wells, etc. The various concepts introduced above and discussed in greater detail below may be implemented in any of numerous ways, as the disclosed concepts are not limited to any particular manner of implementation. Examples of specific implementations and applications are provided primarily for illustrative purposes.

One example includes a system with a dielectric surface that enables simple incorporation of organic molecules onto a nanostructured resonant cavity. This system demonstrates strongly enhanced interaction of light with organic molecules that are brought to within one hundred nanometers from its macroscopic interface. The dielectric surface, which is patterned with a sub-wavelength, periodic structure, supports a special type of Fano resonance with wave functions extending above it. The delocalized nature of these resonances, their long lifetimes, and the structure's altered spectral density of states (SDOS) causes changes in the organic molecule's spectral and angular radiation pattern compared to the molecule's free-space emission pattern.

Placing molecules close to the surface yields sharp spectral features in the molecules' fluorescence spectra, with an enhancement of the differential radiating power (related to brightness) by a factor of up to $6.3 \times 10^3$. Without being bound by any particular theory, it appears that this enhancement can be attributed to two mechanisms: (1) enhancement of the local excitation field through coupling to a resonance mode in the photonic crystal and (2) enhancement of extraction rate of emitted photons in the far field. A theoretical model, derived below from coupled mode theory (CMT) and Green functions expansion in the basis of Bloch modes, can be used to predict the contribution of each mechanism to the total enhancement. Furthermore, the two enhancement mechanisms also contribute to reduce the lasing threshold by at least an order of magnitude when compared to previous experiments with similar molecules. Photonic crystals exhibiting this special type of Fano resonances can also be used to support lasing by organic dye molecules as discussed in greater detail below.

As understood by those of skill in the art, a Fano resonance is a resonance that arises from interference of a narrow discrete resonance with a broad spectral line or continuum. More specifically, the intensity transmitted or reflected by a Fano resonance exhibits an asymmetric shape with the following functional form:

$$I \propto \frac{(F\nu + \omega - \omega_0)^2}{(\omega - \omega_0)^2 + \nu^2}$$

where $\omega_0$ and $\nu$ are standard parameters that denote the position and width of the resonance, respectively, and $|F| \leq 1$ describes the degree of asymmetry. The Fano resonances in the photonic crystals disclosed here each have a maximum peak and a minimum trough (e.g., as shown in FIGS. 5(b) and (e)).

In photonic crystal slabs, the physical origin of Fano resonances lies in the coupling between the guided modes supported by the slab and external plane waves, which occurs because of the periodic modulation of the dielectric constant. The modes supported by photonic crystals generally fall into two categories: (1) pure modes with infinite lifetimes that lie outside the light cone and (2) resonant modes with finite lifetimes that lie within the light cone and consequently can couple to radiation modes. These lifetimes may also be expressed as quality factors (also known as "Q factors" or simply "Q"), which are measures of how slowly a resonance dissipates energy or, equivalently, how long the resonance stores energy.

There is a special subset of Fano resonances whose quality factors may approach infinity. In theory, in a perfect infinite periodic photonic crystal slab, due to symmetry considerations, Fano resonances at a wave vector of k=0 may completely decouple from the external world with infinite radiative quality factor ($Q_{rad}$) despite lying within the light cone. For k near zero, these guided resonances have ultra-long (but finite) lifetimes, providing an efficient means to couple light in and out of the slab.

Because the guided resonances in these photonic crystals have such long lifetimes, they can be used to resonantly enhance absorption by sources on the surfaces of these photonic crystals. To see how, consider a source, such as an organic molecule or quantum dot, on the surface of such a photonic crystal. If the source has a resonance whose frequency substantial coincides with the photonic crystal's Fano resonance frequency, then the source will excite the photonic crystal's resonance mode, resulting in large local field enhancement near the photonic crystal's surface. This enhanced local field results in increased absorption by the source. In other words, a photonic crystal with a Fano resonance at or near k=0 provides excitation enhancement of incident radiation for the source.

A photonic crystal with a Fano resonance also provides extraction enhancement of the radiation emitted by the source. Suppose that the source radiates in response to absorption of incident radiation—for example, it may fluoresce, phosphoresce, or emit a Raman signal. In free space, the source emits this radiation isotropically. When electromagnetically coupled to the photonic crystal and excited from a first direction, the source radiates preferentially in a second direction instead of radiating isotropically. As a result, the radiant intensity (power per solid angle) goes up in the preferentially illuminated direction. (The radiant intensity goes down in other directions to conserve energy.) Thus, the photonic crystal's Fano resonance causes an angular redistribution of radiation emitted by a source on the crystal's surface. Fano resonances at or near k=0 tend to have high quality factors, leading to even larger enhancement values.

Until now, experimental verification of high-Q Fano resonances at or near k=0 over a macroscopically large area had yet to be demonstrated, possibly because of photonic crystal fabrication and material challenges. One challenge in observing these resonances is that in practical structures, in addition to limits imposed by material absorption, fabrication imperfections may break the crystal symmetry, which results in coupling of these Fano resonances to radiating modes. In addition, extending the mode over a macroscopic area in order to support a higher radiative quality factor poses a significant fabrication challenge.

Photonic Crystals with Fano Resonances for Emission Enhancement

Figure 1B:
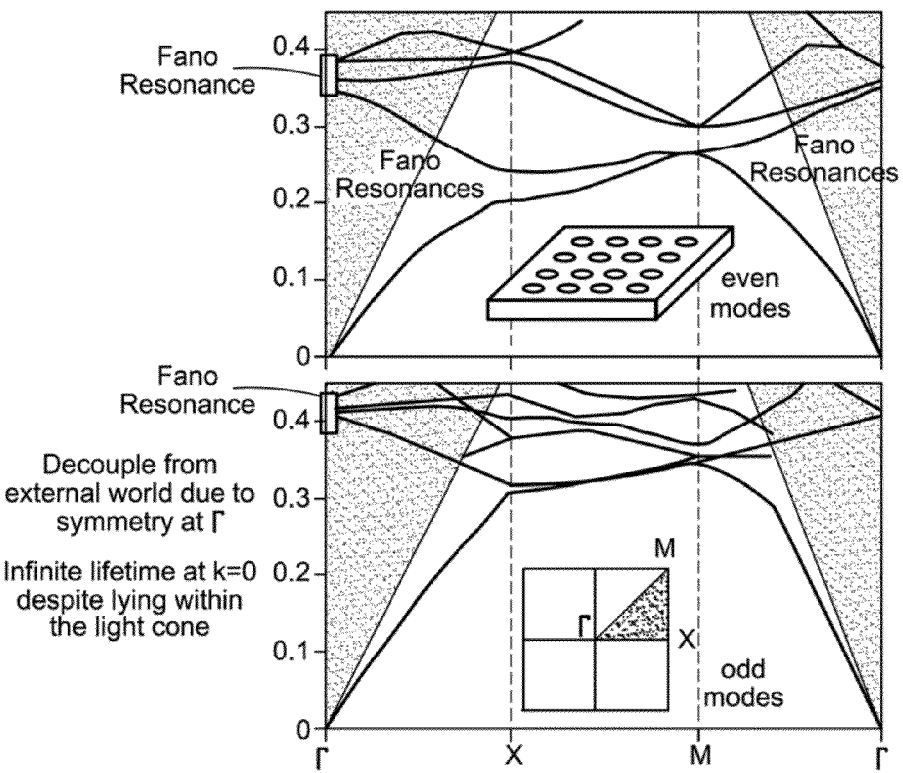
FIG. 1B is a diagram of the energy band structure of the photonic crystal shown in FIG. 1A.

FIG. 1A is a schematic diagram of a large-area, square-lattice photonic crystal 100 whose energy band structure (shown in FIG. 1B) includes a Fano resonance at or near a wave vector of k=0 (i.e., at or near the Γ point). Unlike other photonic crystals with Fano resonances, this photonic crystal 100 is free of defects. Instead, it includes a dielectric substrate 110 with a large area that is uniformly patterned with holes 112 arrayed on a square lattice. FIG. 1A also shows the Fano resonance's egg-crate-like energy density surface 101, which has troughs over the holes 112 and peaks over the dielectric material 114 surrounding the holes 112.

In one example, the substrate 110 includes a 250 nm thick slab of $Si_3N_4$ with periodic cylindrical holes 112 on top of 6 µm thick $SiO_2$ layer. The holes 112 are spaced at an average period of 320 nm, with an average hole diameter of 160 nm and an average hole depth of 55 nm. These uniformly periodic hole patterns may extend over several square centimeters (e.g., 1, 2, 3, 4, or 5 $cm^2$). Those of ordinary skill in the art will readily appreciate that other hole spacings, diameters, and depths are possible, as are slabs of other materials or thicknesses.

Figure 1C:
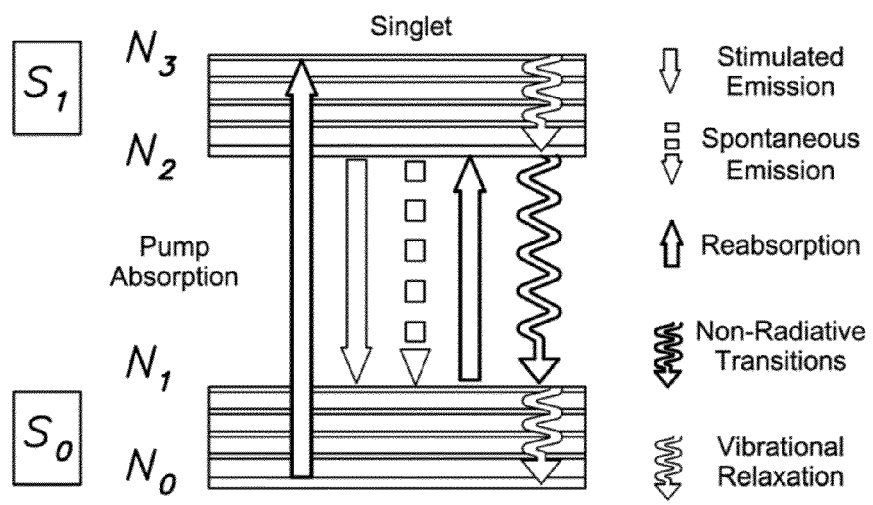
FIG. 1C is a energy level diagram of an organic molecule on the surface of the photonic crystal shown in FIG. 1A.

The dielectric substrate 110 defines a surface 112 to hold one or more resonant sources, such as organic molecules, quantum dots (including organic and inorganic quantum dots), quantum wells, and exciton-hole pairs. In this case, the dielectric substrate 110 supports several emitters—here, organic dye molecules 10—each of which is characterized by the energy level diagram shown in FIG. 1C. For instance, the organic dye molecules 10 may be Rhodamine 6G (R6G) dissolved in methanol at 1 mM concentration and placed on top of the photonic crystal 100. This energy level diagram shows that irradiating one of these dye molecules 10 with pump radiation from a radiation source, which may be a coherent light source (e.g., a laser 120) or an incoherent light source (e.g., a light-emitting diode, a white-light source, a supercontinuum source, etc.), causes the dye molecule 10 to undergo a transition from a lower singlet state $S_0$ to a higher singlet state $S_1$. The excited dye molecule 10 relaxes back to the lower singlet state $S_0$ through stimulated emission, spontaneous emission, non-radiative transitions, and vibrational transitions. It may also reabsorb the emitted radiation.

A detector, such as a spectrometer 130, senses the radiation (e.g., fluorescence) emitted by the organic molecule(s) illuminated by the laser 120. The spectrometer 130 may use the detected signal to determine the fluorescence spectrum of the organic molecule(s), which in turn can be used to identify the organic molecules 10. For instance, the photonic crystal 100, laser 120, and spectrometer 130 may be used for fluorescence spectroscopy or Raman spectroscopy: the laser 120 illuminates the organic molecule 10 at the appropriate frequency, causing the molecule 10 to emit fluorescent light or a spontaneous or stimulated Raman scattering signal. The spectrometer 130 determines the spectrum of this emitted light; as understood by those of skill in the art, this spectrum may be used to identify the molecule.

As mentioned above, the photonic crystal 100 enhances the signal emitted by the organic molecule 10. This enhancement results in an increase in the intensity of the signal measured by the detector 130 (assuming that the laser 120 and the detector 130 are properly aligned). Without being bound by any particular theory, it appears that two mechanisms provide this enhancement: (1) the photonic crystal's resonant absorption and subsequent dissipation of the incident laser light provides excitation enhancement and (2) the photonic crystal's modified spectral density of states provides extraction enhancement by restricting the molecule's fluorescence emission to a relatively small solid angle.

Excitation enhancement occurs in structures that support resonances for the excitation wavelength via enhancement of the local electric field in the site of the molecules. In many nanostructured resonances, the active volume of the organic material that interacts with the resonance is small (compared to the wavelength), so only a small fraction of the excitation beam is absorbed. However, the local excitation field can be orders of magnitude higher than in free space when the pump is coupled to resonances with long lifetimes (the pump resonant modes). This coupling leads to enhanced absorption. The power absorbed by bulk molecules is given by $P^B_{abs} = (N_0 \sigma_{abs} d) P_{in}$, where $\sigma_{abs}$ is the absorption cross-section of molecules at the excitation wavelength, $N_0$ is the number density of molecules, d is the thickness of the layer that the molecules occupy and $P_{in}$ is the pump power. Through coupled mode theory, the absorption enhancement in a layer of thickness $d^P_{eff}$ coupled to a resonant pump mode compared to bulk absorption is given by:

$$\Lambda_C \equiv \frac{P^{res}_{abs}}{P^B_{abs}} = \frac{2\lambda^P}{\pi n d^P_{eff}} \frac{\alpha^P (Q^P)^2}{Q^P_r} \quad (1)$$

where $\lambda^P$ is the pump wavelength, n is the refractive index of the liquid in which the organic molecules are dissolved, $Q^P_r$ and $Q^P$ are the radiative and total quality factors, respectively, of the pump mode, $d^P_{eff}$ is the length of the evanescent tail of the pump mode into the molecule layer, and $\alpha^P$ is the energy confinement of the pump mode in the molecule layer. The quantities in Equation (1) can be found either by finite-difference time-domain (FDTD) simulation or reflection measurements. The maximum extraction enhancement occurs when the Q-matching condition between the radiative and non-radiative quality factors is satisfied.

Extraction enhancement is due to the strong modification of the spectral density of states (SDOS) in the presence of a Fano resonance. Coupling the molecules to a macroscopic nanostructure resonance dramatically alters the molecules' angular emission compared to free-space emission. When coupled to a resonance, the rate at which a uniform and isotropic collection of molecules generates photons with crystal momentum k at a resonant frequency $\omega_k$ can be written as:

$$\Gamma^{PhC}(k, \omega_k) = \frac{N_0 \pi \omega_k |\mu|^2}{3\hbar \epsilon_0} \alpha^F(k, \omega_k) \times S(k, \omega_k) \quad (2)$$

This result can be achieved by expanding the Green function with a basis of normalized Bloch modes, $E_{k\omega\_k(r)}$, with finite lifetimes characterized by the total quality factor $Q^F_{tot}(k, \omega_k) = \omega_k/(2\Delta\omega_k)$. Here, $\alpha^F_{k,\omega\_k}$ is the energy confinement of the fluorescence resonance mode in the molecule layer, $S(k, \omega_k) = A/(4\pi^3 \Delta\omega_k)$ is the SDOS at the resonance $\omega_k$ crystal momentum k, A is the area of the macroscopic Fano resonance, and $|\mu|$ is the electric dipole momentum of the molecules. The extraction enhancement into the far field when on photonic crystal compared to in free-space under the assumption that the radiation direction is close to normal direction can be written as:

$$\Lambda_T(k, \omega_k) = \frac{\Gamma^{PhC} \times \frac{Q^F}{Q^F_r}}{\Gamma^{f-s}} = \frac{\lambda^F \alpha^F}{n\pi d^F_{eff}} \frac{(Q^F)^2}{Q^F_r} \quad (3)$$

where $d^F_{eff}(k, \omega_k)$ is the effective length of the evanescent tail of the fluorescence mode in the molecule layer and $Q^F_r(k, \omega_k)$ is the radiative quality factor of the fluorescing channel. Like the quantities in Equation (1), the quantities in Equation (3) can be obtained from FDTD calculations and reflection measurements.

Equation (3) shows that increasing enforcing the Q-matching condition of $Q_{nr}(k, \omega_k) = Q^{tot}_r(k, \omega_k)$ increases the extraction enhancement, just it increases the excitation enhancement. Increasing the energy confinement of the fluorescence resonance mode in the molecule layer also increases the extraction enhancement.

There are three major differences between this formalism and local density of states (LDOS) enhancement calculations in micro-cavity systems:
(1) this formalism deals with the emission from a uniform and isotropic ensemble of molecules placed on a periodic macroscopic photonic crystal into a fixed crystal momentum k at $\omega_k$, which is proportional to the system's SDOS instead of to the LDOS (which is proportional to the emission of one dipole into all directions);
(2) this formalism treats an infinitely large system by expanding Green functions with a basis of Bloch modes under periodic boundary condition instead of localized eigenmodes as often used in LDOS calculations; and
(3) this formalism accounts for the photons that are radiated coherently to the far field and reach.
As a result, the maximizing condition changes from maximizing $Q_{tot}$ in general to enforcing the Q-matching condition.

Given knowledge of the local excitation and extraction enhancement, the total enhancement factor can be approximated as the product of the excitation and extraction enhancement factors:

$$\Lambda(k, \omega_k) = \frac{\eta_{PhC}}{\eta_0} \frac{2\lambda^P \lambda^F}{\pi^2 n^2 d^P_{eff} d^F_{eff}} \frac{(Q^P)^2}{Q^P_r} \frac{(Q^F)^2}{Q^F_r} d^P_{eff} a^2 \underbrace{\int_{gain} |E^F(r)|^2 |E^P(r)|^2 \, dr}_{overlap\ integral} \quad (4)$$

$$\approx \Lambda_C \Lambda_T(k, \omega_k)$$

This approximation is valid under two conditions: (1) the quantum yield of the molecules remains constant, and (2) the normalized pump and fluorescence mode profiles are roughly uniformly distributed in a similar region in space, meaning the overlap integral in Equation (4) can be simplified as the product of the fraction of pump mode energy in the molecule layer and the energy confinement of the fluorescence resonance mode in the molecule layer. The latter approximation is commonly ignored, but can lead to further enhancement.

These two enhancement mechanisms may also reduce the lasing threshold of a source (e.g., one or more organic molecules) on the surface of a photonic crystal for at least two reasons. First, the excitation field is dramatically enhanced near the surface of the photonic crystal. This enables substantial absorption of the pump within a thin layer of diluted molecules near the photonic crystal surface. Second, placing the molecules on the photonic crystal's surface enhances the molecules' emission rate into the lasing mode compared to their free-space emission in a similar modal volume. This enhancement can be introduced phenomenologically into the lasing rate equation through the spontaneous emission factor, $\beta$, which is classically defined as the ratio between the emission rate into the lasing mode and the total emission rate. The lasing threshold is typically inversely proportional to $\beta$ and hence can be reduced in cases where the emission rate into the lasing mode is enhanced while the total rate remains almost constant.

Photonic Crystals with Fano Resonances for Quantum Yield Enhancements

Apart from on-resonance coupling effects, the radiative decay rates of a molecule placed on the surface of an inventive photonic crystal may be altered significantly while coupled to a Fano resonance supported by the inventive photonic crystal. Therefore, the molecule's far field emission signal is stronger and its quantum yield is greater on the photonic crystal's surface than on the surface of a bulk dielectric material.

The increase in the averaged enhancement of the radiative decay rate and quantum yield depends on the photonic crystal's band structure, the signals' frequency distribution, the original quantum yield enhancement, etc. For a uniform collection of randomly polarized dipoles placed on top of a photonic crystal surface, the average enhancement of radiative decay rate (also known as the local Purcell enhancement) can be estimated as:

$$F_p(r) \equiv \frac{\Gamma_r^{PhC}}{\Gamma^0} = \frac{3}{4\pi^2} \frac{\omega}{\Delta\omega} \frac{|E(r)|^2}{|E^0|^2} + 1$$

where $\omega$ is the center frequency of the signal, which is also assumed to be the center of the resonance frequency; $\Delta\omega = \max\{\Delta\omega_R; \Delta\omega_S\}$ where $\Delta\omega_R$ is the linewidth of resonance and $\Delta\omega_S$ is the linewidth of the source signal; and $$\frac{|E(r)|^2}{|E^0|^2}$$

is the local field enhancement due to the resonance. With this in mind, the spatially averaged Purcell enhancement can be written as:

$$\overline{F_p} \equiv \frac{\overline{\Gamma_r^{PhC}}}{\Gamma^0} \approx \frac{3}{4\pi^2} \frac{A_k(\Delta\omega)}{(2\pi/a)^2} \frac{\omega}{\Delta\omega} \frac{\alpha\lambda^3}{a^2 d_{eff}} + 1$$

where $\lambda$ is the center wavelength of the source and the resonance; $d_{eff}$ is the effective length of the evanescent tail of the resonance; a is the photonic crystal's periodicity; and $$\frac{A_k(\Delta\omega)}{(2\pi/a)^2}$$

is the portion of one full Brillouin zone with photonic crystal resonance frequencies within the source's signal range.

To increase the spatially averaged Purcell enhancement, one can: (1) increase the portion of the Brillouin zone within the source's signal range; (2) match the center frequency of resonance to that of the source; and (3) match the quality factor of the resonances $$Q_R = \frac{\omega_0}{\Delta\omega_R}$$

to the quality factor of the source $$Q_S = \frac{\omega_0}{\Delta\omega_S}.$$

Accordingly, the quantum yield enhancement can be written as:

$$\Lambda_\eta \equiv \frac{\eta_{PhC}}{\eta_0} = \frac{\overline{F_p}}{\eta_0 \overline{F_p} + (1-\eta_0)}$$

This expression can be used to estimate the quantum yield enhancement for different photonic structures as explained below.

Figure 1D:
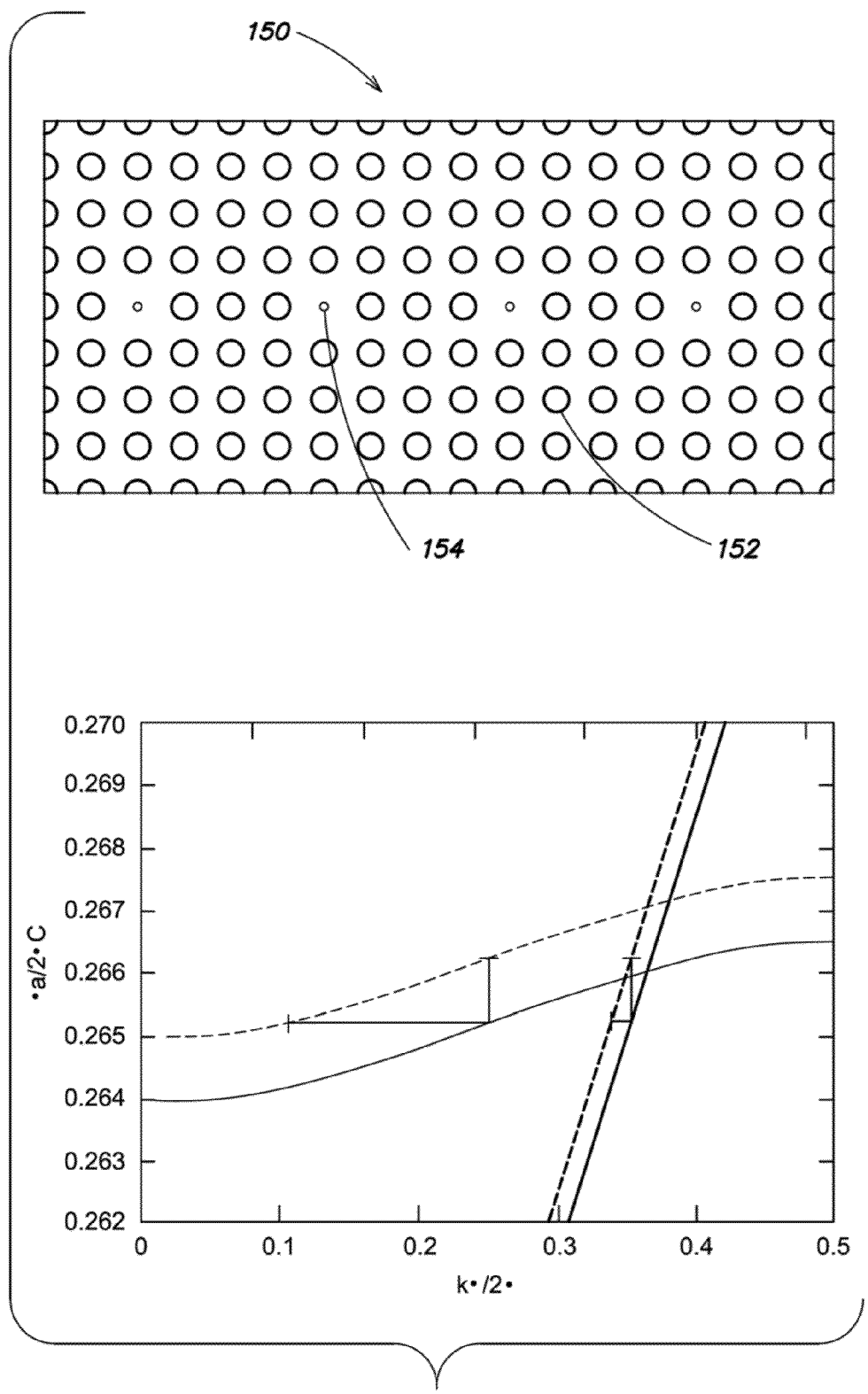
FIG. 1D illustrates a photonic crystal with linear defects (left) and its photonic band structure (right).

FIG. 1D shows a photonic crystal 150 (left) comprising a square lattice of high-∈ dielectric rods 152 ($\in_H$=12.25) embedded in a low-∈ dielectric material ($\in_L$=2.25). The lattice spacing is denoted a, and the radius of each rod is r=0.25a. This photonic crystal is known as a coupled-cavity waveguide, or coupled resonator optical waveguides, because it includes many cavities 154 formed by reducing the radius of every fourth rod along one row of the array to r/3 to give a supercell period 4a. When isolated, each of these cavities supports a resonant mode with a resonant frequency well inside the bandgap. Bringing such cavities close to each other to form a linear defect, as shown in FIG. 1D, enables photons to propagate down the defect by tunneling from one cavity to another. Consequently, the group velocity is small; the less closely coupled the cavities are, the slower the group velocity. Group velocities of c/1000 or even smaller are easy to attain in such systems.

The plot at right in FIG. 1D shows the induced change in the photonic band frequency for the CCW photonic crystal. In particular, it shows the effect of induced refractive index changes for two dispersion curves: the slow-light band with $v_G$=0.022c used in the photonic crystal at left (sine-like solid curve) and the dispersion curve of a uniform material with n=3.5 (nearly vertical solid curve). Applying the same frequency shift (dv 5 0.001) to both dispersion curves yields the respective dashed curves, which exhibit different changes in wave vector for identical frequency shifts.

Figure 1E:
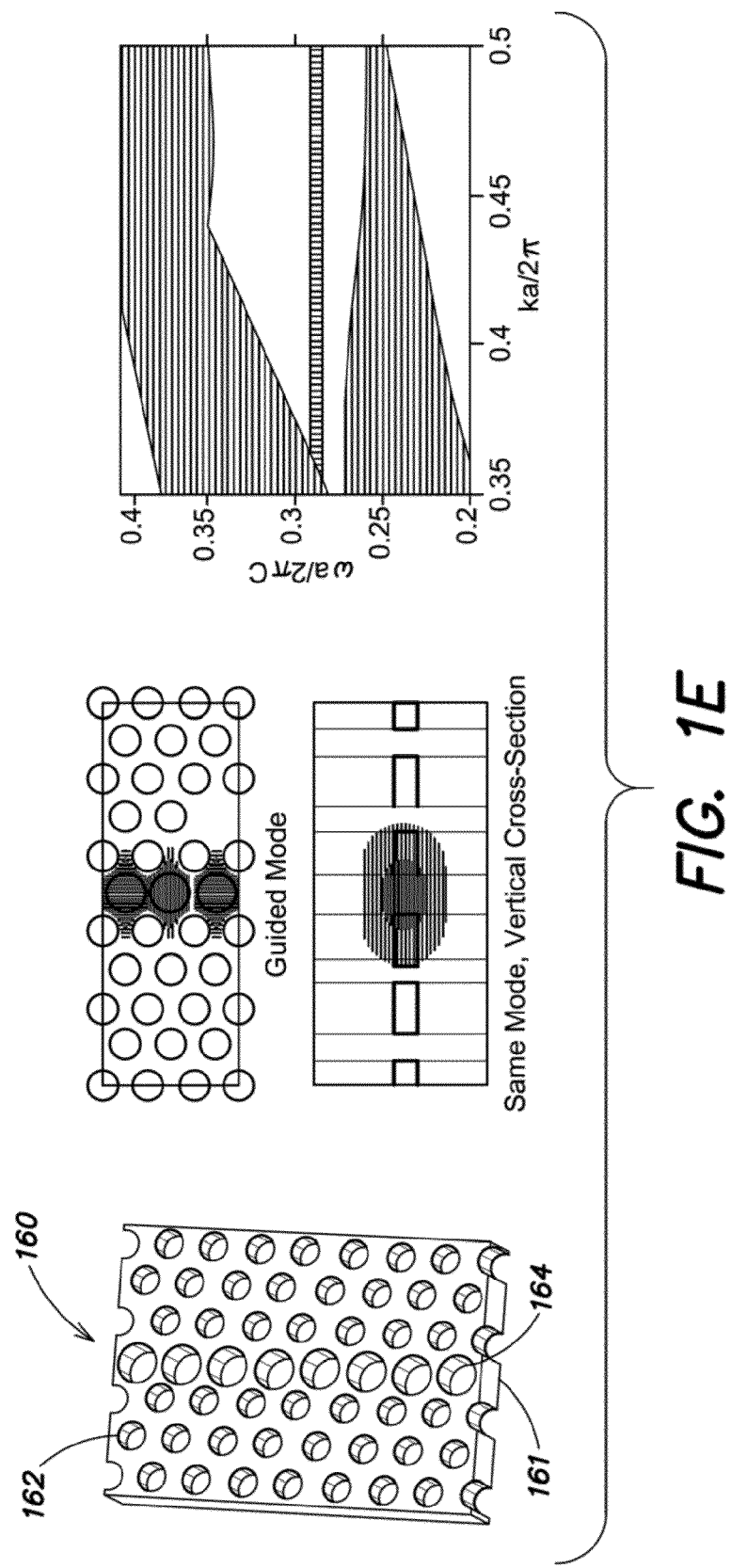
FIG. 1E illustrates another photonic crystal with linear defects (left), its guided mode (center), and its photonic band structure (right).

FIG. 1E shows another CCW photonic crystal 160 (left) formed by patterning holes 162 in a dielectric slab 161. Holes 164 arrayed along one column are enlarged to form a coupled-cavity waveguide. The central image in FIG. 1E illustrates the guided mode, and the plot at right illustrates the CCW photonic crystal's photonic band structure.

The averaged Purcell enhancement and quantum yield enhancement for the photonic crystals in FIGS. 1D and 1E can be written, respectively, as:

$$\overline{F_p} \equiv \frac{\overline{\Gamma_r^{PhC}}}{\Gamma^0} \approx \frac{3}{4\pi^2} \frac{L_k(\Delta\omega)}{2\pi/a} \frac{\omega}{\Delta\omega} \frac{\alpha\lambda^2}{a d_{eff}} + 1 < \frac{3}{4\pi^2} \frac{1}{N} \frac{\omega}{\Delta\omega} \frac{\alpha\lambda^2}{a d_{eff}} + 1$$

$$\Lambda_\eta \equiv \frac{\eta_{PhC}}{\eta_0} = \frac{\overline{F_p}}{\eta_0 \overline{F_p} + (1-\eta_0)}$$

where $L_k(\Delta\omega)$ is the length in 1D k-space with frequency within the signal frequency range and N is the number of basic unit cells in the super-cell.

Figure 1F:
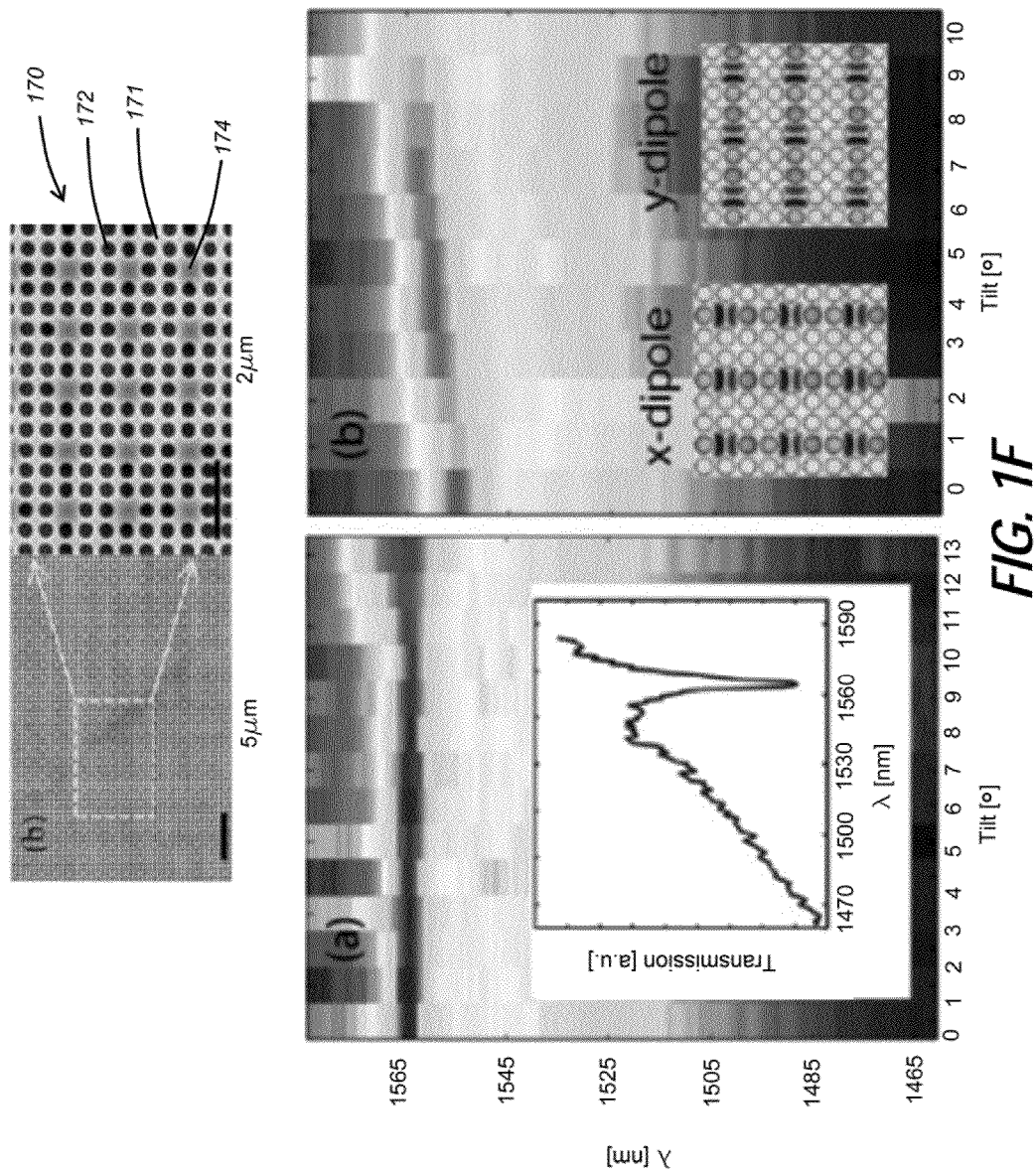
FIG. 1F illustrates a multiply periodic photonic crystal (left) and its photonic band structure (right).

FIG. 1F shows a coupled resonator photonic crystal 170 with holes 172 on a first square lattice of period a in a dielectric slab 171. This photonic crystal 170 also includes filled holes 174 arranged on second square lattice of period 3a that is aligned with the first square lattice. The plots at right in FIG. 1F illustrate experimental measurements of this photonic crystal's band structure. The averaged Purcell enhancement and quantum yield enhancement for the photonic crystal 170 in FIG. 1F can be written, respectively, as:

$$\overline{F_p} \equiv \frac{\overline{\Gamma_r^{PhC}}}{\Gamma^0} \approx \frac{3}{4\pi^2} \frac{A_k(\Delta\omega)}{(2\pi/a)^2} \frac{\omega}{\Delta\omega} \frac{\alpha\lambda^3}{a^2 d_{eff}} + 1 < \frac{3}{4\pi^2} \frac{1}{N} \frac{\omega}{\Delta\omega} \frac{\alpha\lambda^3}{a^2 d_{eff}} + 1$$

$$\Lambda_\eta \equiv \frac{\eta_{PhC}}{\eta_0} = \frac{\overline{F_p}}{\eta_0 \overline{F_p} + (1-\eta_0)}$$

where N is the number of basic unit cells in the super-cell (the photonic crystal 170 shown in FIG. 1F includes nine basic unit cells per super-cell).

Figure 1G:
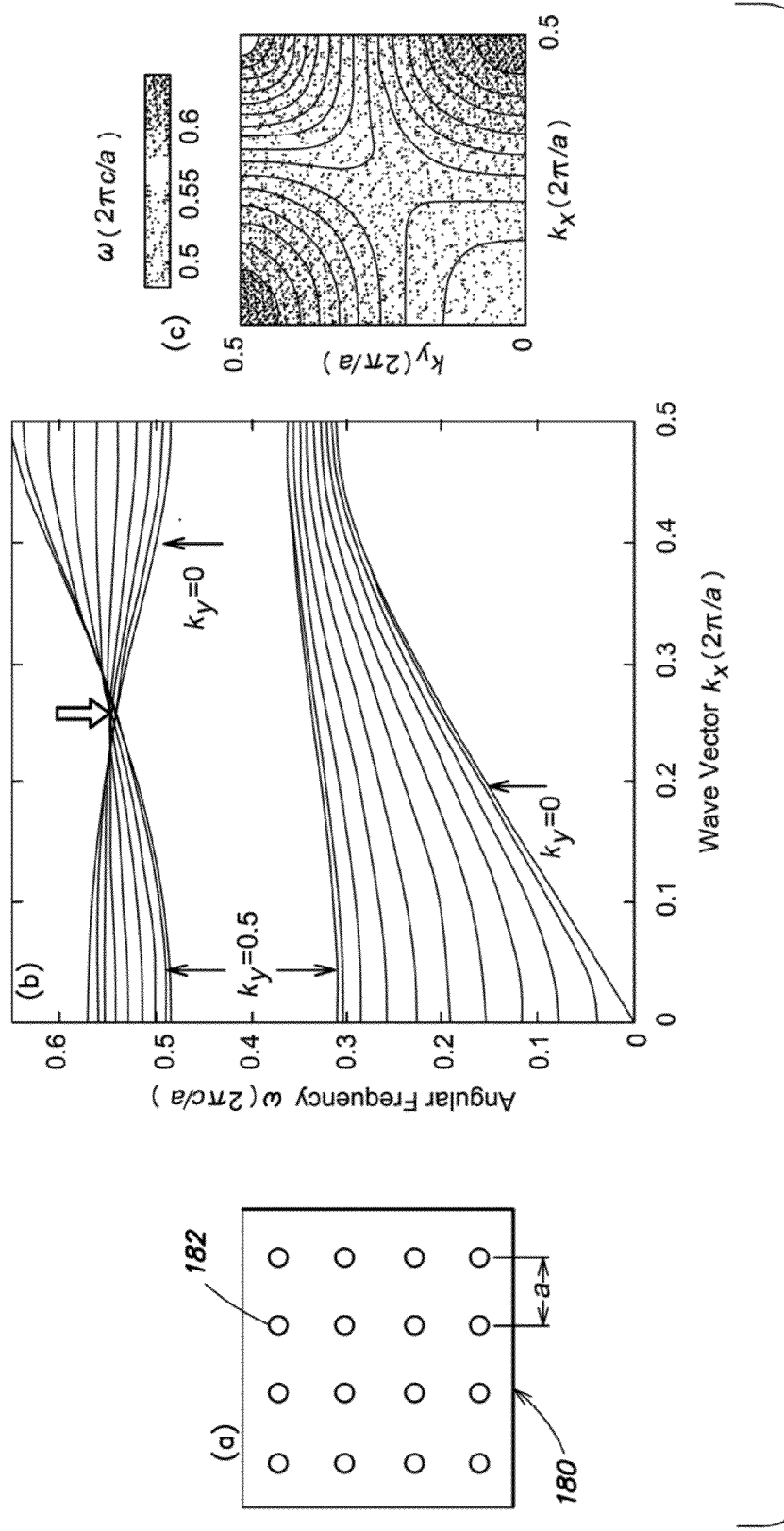
FIG. 1G illustrates a uniformly periodic photonic crystal (left) and its photonic band structure (right).
Figure 1H:
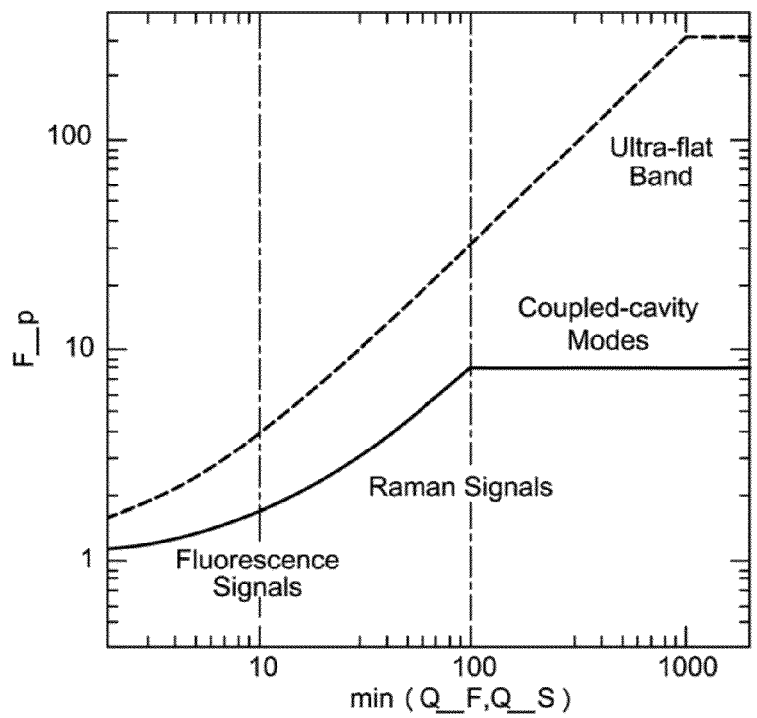
FIG. 1H is a plot of the Purcell enhancement for photonic crystals with ultra-flat bands (upper curve) and coupled-cavity modes (lower curve).
Figure 1I:
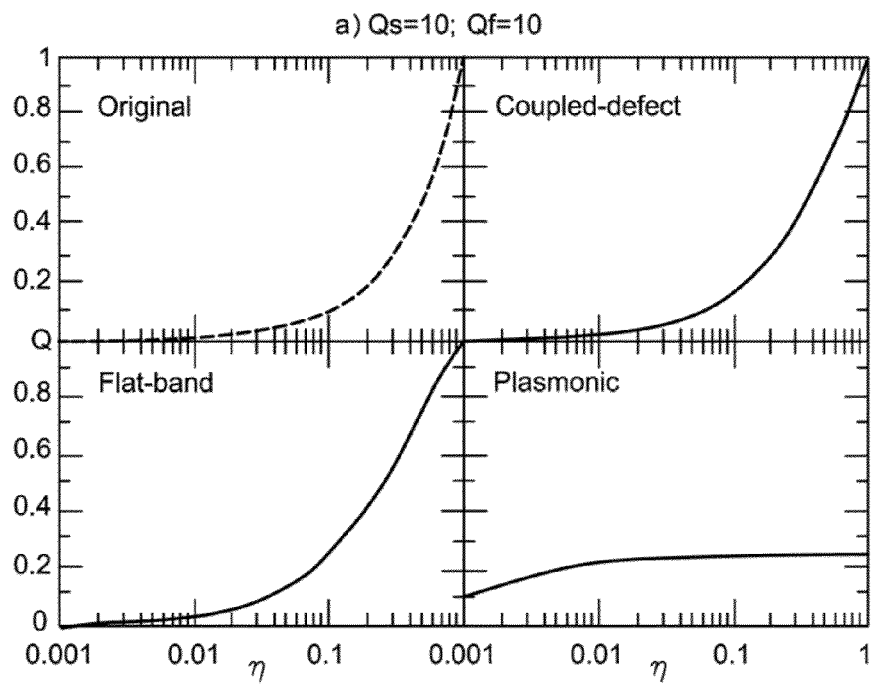
FIGS. 1I, 1J, and 1K shows plots of quantum yield for flat-band, coupled-defect, plasmonic, and conventional photonic crystals for quality factors of 10, 100, and 1000, respectively.
Figure 1J:
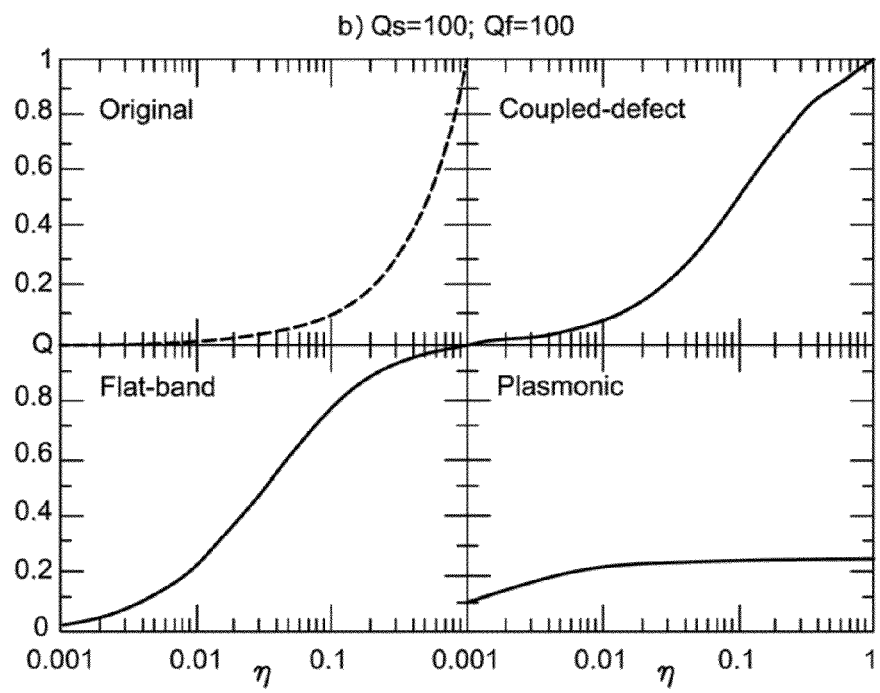
Figure 1K:
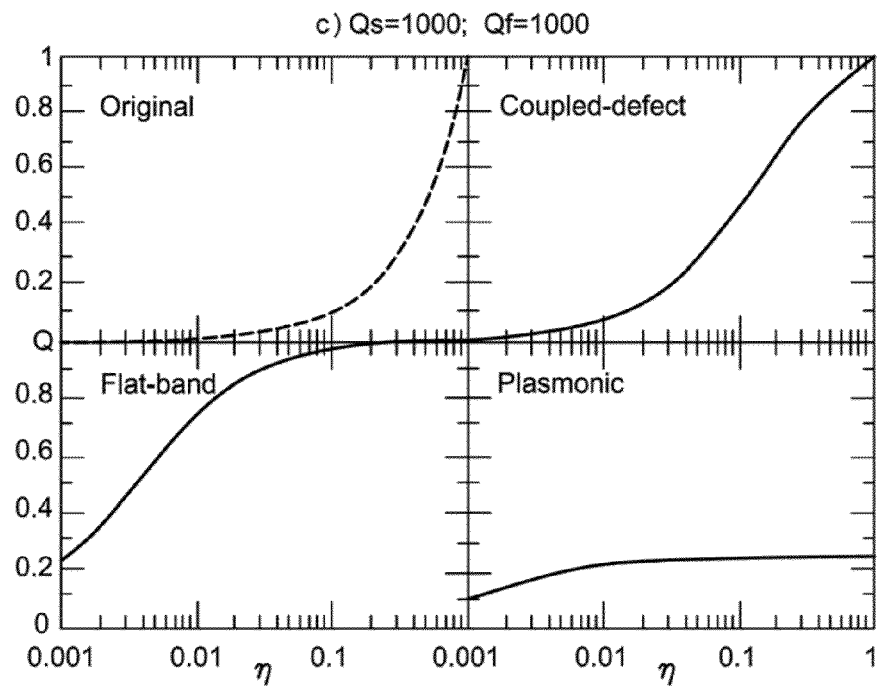

FIG. 1G shows a photonic crystal 180 formed by square lattice of rods 182 with an index of refraction n=3.4 and radius r=0.134a. The plot at the center of FIG. 1G is the p projected transverse magnetic band structure of the photonic crystal 180. The black lines represent $\omega(k_x)$ curves at fixed $k_y$ values ranging from $k_y$=0 to $k_y$=0.5(2π/a) in steps of 0.05(2π/a). The thick arrow indicates an ultra-flat cross-section of the second band. The contour plot at right in FIG. 1G illustrates the second band $\omega(k_x, k_y)$. The saddle point and its principal axes are indicated by the black dot at the center of the plot. The extended ultra-flat band is along the dashed line.

For a flat band (e.g., a band whose variation with frequency is less than or equal to about 20% to about 30% over the Brillouin zone), the averaged Purcell enhancement and quantum yield enhancement can be written, respectively, as:

$$\overline{F_p} \equiv \frac{\overline{\Gamma_r^{PhC}}}{\Gamma^0} \approx \frac{3}{4\pi^2} \frac{A_k(\Delta\omega)}{(2\pi/a)^2} \frac{\omega}{\Delta\omega} \frac{\alpha\lambda^3}{a^2 d_{eff}} + 1$$

$$\Lambda_\eta \equiv \frac{\eta_{PhC}}{\eta_0} \approx \frac{\overline{F_p}}{\eta_0 \overline{F_p} + (1-\eta_0)}$$

For the flat second band in FIG. 1G, this yields a Purcell enhancement of about 1.3, which is also close to quantum yield enhancement.

For a 1D grating photonic crystal with a saddle point in its band structure (e.g., the saddle point dispersion shown in FIG. 1G), the estimated averaged Purcell enhancement and quantum yield enhancement are:

$$\overline{F_p} \equiv \frac{\overline{\Gamma_r^{PhC}}}{\Gamma^0} \approx \frac{3}{4\pi^2} \ln\left(\frac{\omega}{\Delta\omega}\right) \frac{\alpha\lambda^3}{a^2 d_{eff}} + 1$$

$$\Lambda_\eta \equiv \frac{\eta_{PhC}}{\eta_0} \approx \frac{\overline{F_p}}{\eta_0 \overline{F_p} + (1-\eta_0)}$$

For a general photonic crystal with a flat-band structure, the enhancements can be written as:

$$\overline{F_p} \equiv \frac{\overline{\Gamma_r^{PhC}}}{\Gamma^0} \approx \frac{3}{4\pi^2} \frac{A_k(\Delta\omega)}{(2\pi/a)^2} \frac{\omega}{\Delta\omega} \frac{\alpha\lambda^3}{a^2 d_{eff}} + 1 \le \frac{3}{4\pi^2} \frac{\omega}{\Delta\omega} \frac{\alpha\lambda^3}{a^2 d_{eff}} + 1$$

$$\Lambda_\eta \equiv \frac{\eta_{PhC}}{\eta_0} \approx \frac{\overline{F_p}}{\eta_0 \overline{F_p} + (1-\eta_0)}.$$

FIGS. 1H-1K are plots of the final averaged Purcell enhancement and final quantum yield derived by defining different starting conditions of $$Q_R = \frac{\omega_0}{\Delta\omega_R},\; Q_S = \frac{\omega_0}{\Delta\omega_S},\; Q_F = \frac{\omega_0}{\Delta\omega_F},$$

and $\eta_0$. Here, $$Q_F = \frac{\omega_0}{\Delta\omega_F}$$

represents the flatness of the band, with $\Delta\omega_F$ being the largest frequency deviation from the center frequency within the Brillion zone.

The extraction enhancement and excitation enhancement are independent of each other. The expressions above are for extraction enhancement. Combining these extraction expressions with excitation enhancement expressions yields the total enhancement:

$$\Lambda_{tot} = \int_{gain} \Lambda_c(\vec{r})\Lambda_\eta(\vec{r}) d\vec{r} \times \overline{\left(\frac{Q_R}{Q_r}\right)}$$

$$\Lambda_c(\vec{r}) = \frac{2\lambda^P}{\pi n d_{eff}} \frac{(Q^P)}{Q_r^P} |E^P(\vec{r})|^2$$

when the photonic crystal is pumped on-resonance. Here, $Q_R$ is the quality factor of the resonances; $Q_r$ is the radiative quality of the resonance; and ratio $Q_R/Q_r$ represents the averaged chance of generated photons can reach far field while coupled to the photonic crystal resonances.

Photonic Crystals with Fano Resonances for Raman Scattering Enhancements

Photonic crystals with flat dispersions can also be use to enhance Raman scattering signals. One difference between fluorescence and Raman scattering enhancement is that the fluorescence is a multi-step process, whereas Raman scattering is an instantaneous process. Therefore, increasing the radiative decay rate may not affect absorption cross-section for fluorescence; however, it may affect the Raman scattering cross section. For similar multi-step processes, the total enhancement may be predicted as above, whereas the total enhancement for instantaneous processes can be written as follows:

$$F_p(r) \equiv \frac{\Gamma_r^{PhC}}{\Gamma^0} = \frac{3}{4\pi^2} \frac{\omega}{\Delta\omega} \frac{|E(r)|^2}{|E^0|^2} + 1$$

$$\Lambda_c(\vec{r}) = \frac{2\lambda^P}{\pi n d_{eff}} Q^P |E^P(\vec{r})|^2$$

$$\Lambda_{tot} = \int_{gain} \Lambda_c(\vec{r}) F_p(\vec{r}) d\vec{r} \approx \Lambda_C \overline{F_P}$$

$$\overline{F_p} \equiv \frac{\overline{\Gamma_r^{PhC}}}{\Gamma^0} \approx \frac{3}{4\pi^2} \frac{A_k(\Delta\omega)}{(2\pi/a)^2} \frac{\omega}{\Delta\omega} \frac{\alpha\lambda^3}{a^2 d_{eff}} + 1$$

The fluorescence examples in the preceding section can also be used to estimate Raman scattering enhancement by replacing the appropriate parameters in the above equations.

Photonic Crystal-Based Raman Spectroscopy System

Figure 2A:
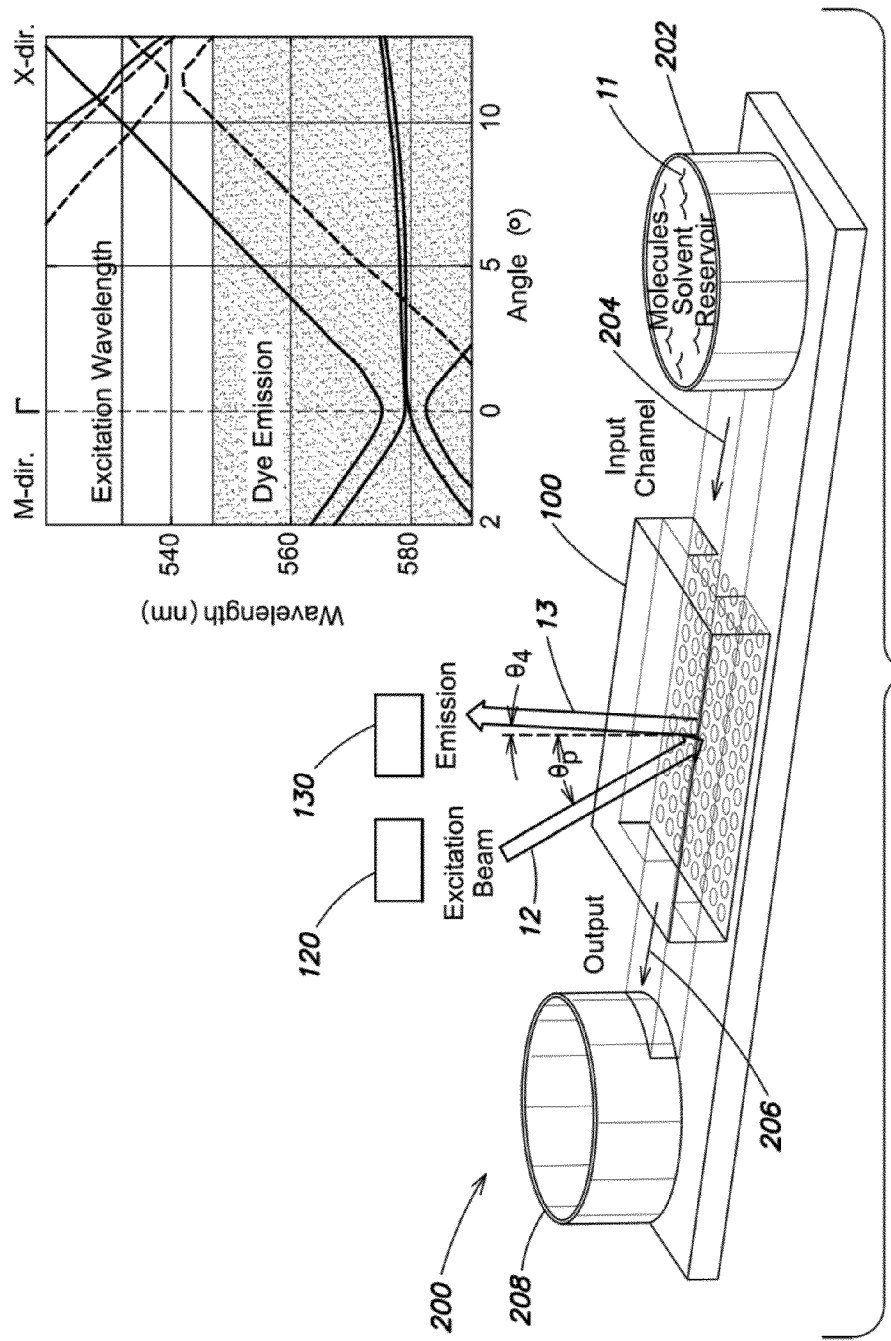
FIG. 2A illustrates a system for enhancing radiation emitted by a source flowing over the surface of the photonic crystal shown in FIG. 1A.

FIG. 2A illustrates a spectroscopy system 200 based on the photonic crystal 100 shown in FIG. 1A. The spectroscopy system 200 includes a first reservoir 202 that holds one or more emitters (not shown), such as organic molecules or quantum dots, in solution 11. This solution 11 flows along an input channel 204 across a photonic crystal 100 whose energy band structure exhibits a Fano resonance as described above. A coherent light source 120 illuminates the particles in the solution 11 and the photonic crystal 100 with an excitation beam 12 that is resonant with both the photonic crystal's Fano resonance and the particles. The particles respond to this excitation by emitting an enhanced emission 13 towards a detector 130, which generates an electrical signal, such as a photocurrent, proportional to the intensity of the detected emission 13. The solution 11 flows off the photonic crystal 100 into an optional second reservoir 208 via an output channel 206.

If desired, the photonic crystal 100, coherent source 120, and 130 may be mounted on translation or rotation stages so that they can be moved or rotated relative to each other, e.g., to optimize enhancement of the particles' emission. In addition, the coherent source 120 may be a tunable source, such as an external-cavity diode laser or tunable fiber laser, whose output 12 can be tuned on or off resonance. This tuning can be accomplished with by feeding back the detector's output to an appropriate control circuit, such as a proportional-integral-derivative controller or an optimization circuit.

Consider, for instance, Raman spectroscopy of an organic molecule using the system 200 shown in FIG. 2A. In Raman spectroscopy, exciting the molecule at a first frequency causes the molecule to emit scattered photons—the Raman signal—at a second frequency. Picking the incident angle to be on-resonance with the pump wavelength maximizes the excitation enhancement. And picking the second frequency to match the frequency corresponding to the photonic crystal's angle of maximum extraction enhancement maximizes the extraction enhancement. These frequencies, along with the angle of maximum extraction enhancement, can be determined by:

(1) identifying the angle of maximum extraction enhancement;
(2) determine the frequency corresponding to the angle of maximum extraction enhancement (e.g., as in the inset of FIG. 8);
(3) selecting the Raman frequency to be on-resonance (i.e., substantially equal to the frequency corresponding to the angle of maximum extraction enhancement);
(4) selecting the pump frequency corresponding to the Raman frequency; and
(5) selecting the pump beam's incidence angle such that the pump frequency is substantially equal to the frequency of the photonic crystal's Fano resonance.

Illuminating the molecule (and the photonic crystal) at the resulting incidence angle and pump frequency leads to resonant pumping and maximum enhancement. Changing the pump beam's incident angle, frequency, or both away from the values determined according to this process tunes the pump off-resonance.

Solar Concentrators Based on Photonic Crystal

Figure 2B:
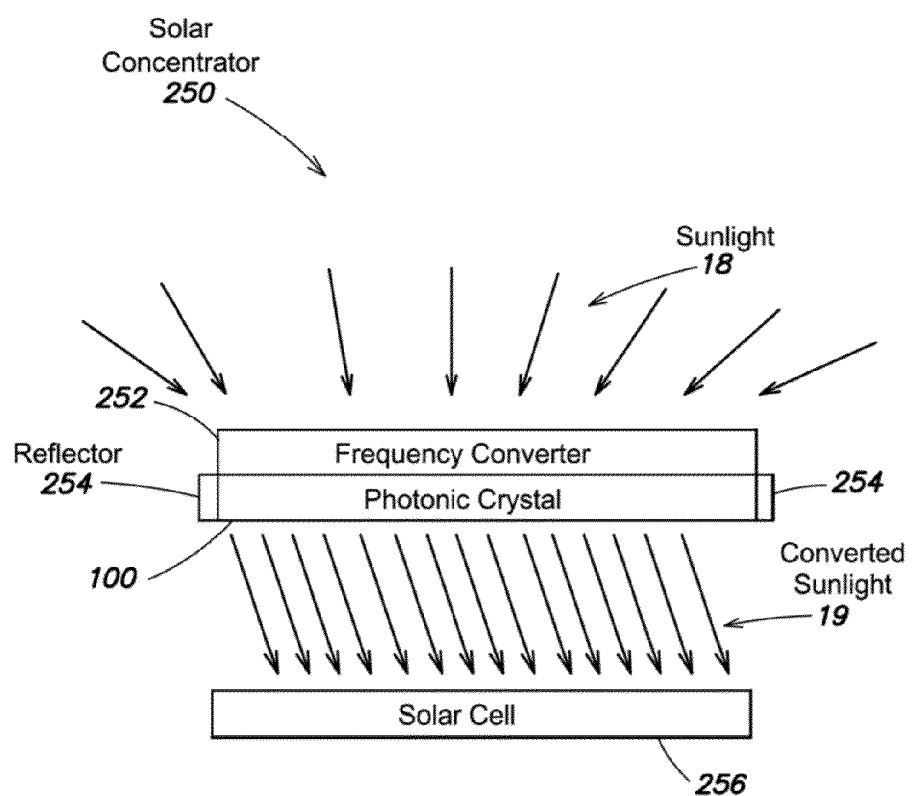
FIG. 2B illustrates a solar concentrator using the photonic crystal shown in FIG. 1A.

FIG. 2B illustrates a solar concentrator 250 that includes a photonic crystal 100 whose energy band structure includes a Fano resonance at or near the Γ point. Sunlight 18 illuminates a frequency converter 252 on top of the photonic crystal 100 over a range of angles. The frequency converter 252, which may include a phosphorescent, fluorescent, or nonlinear optical material, up- or down-converts the incident sunlight to a different frequency. For instance, the frequency converter 252 may comprise phosphorescent material that emits radiation over a relatively narrow range of wavelengths (or even a single wavelength) when illuminated with sunlight 18 or light from a broadband source.

The frequency-converted sunlight 19 emitted by the frequency converter 252 propagates into the photonic crystal, which transmits it to a solar cell 256, such as photovoltaic cell. Optional reflectors 254 on the photonic crystal's edges couple stray photons back into the photonic crystal 100. More precisely, the frequency converter's emission couples to the photonic crystal's resonance(s) and radiates according to the spectral density of states as explained above. Because the photonic crystal's spectral density of states is modified with respect to that of free space, the photonic crystal 100 transmits the frequency-converted sunlight 19 preferentially in one direction as shown in FIG. 2B. The solar cell 256 is arranged to capture substantially all of this frequency-converted sunlight 19. As a result, the solar cell 256 operates with relatively high efficiency.

Methods of Fabricating Highly Uniform Photonic Crystals with Fano Resonances

High quality-factor resonances in a photonic nano-structure depends on consideration of the structure's bulk material properties and its sub-wavelength geometry. Material absorption sets the upper bound of the attainable quality factor, while the structure geometry can be optimized to minimize Rayleigh scattering due to surface roughness. One favorable candidate for achieving high quality factor resonances in the visible portion of the electromagnetic spectrum is a slab of $Si_3N_4$ deposited on top of microns-thick oxide layer of a silicon wafer. With refractive index of 2.02, $Si_3N_4$ provides sufficient index contrast with the $SiO_2$ below and air or fluid on top. Other suitable materials include, but are not limited to SiN, $TiO_2$, GaAs, and AlGaAs.

The uniformity of the photonic crystal's periodic pattern of holes also affects the quality factor of the photonic crystal's resonance(s). In general, the holes' diameters, spacings, and depths should match as closely as possible over as large an area as possible for maximum quality factors (and maximum enhancement). In practice, however, it can be difficult to etch uniform holes over a large area.

Figure 3:
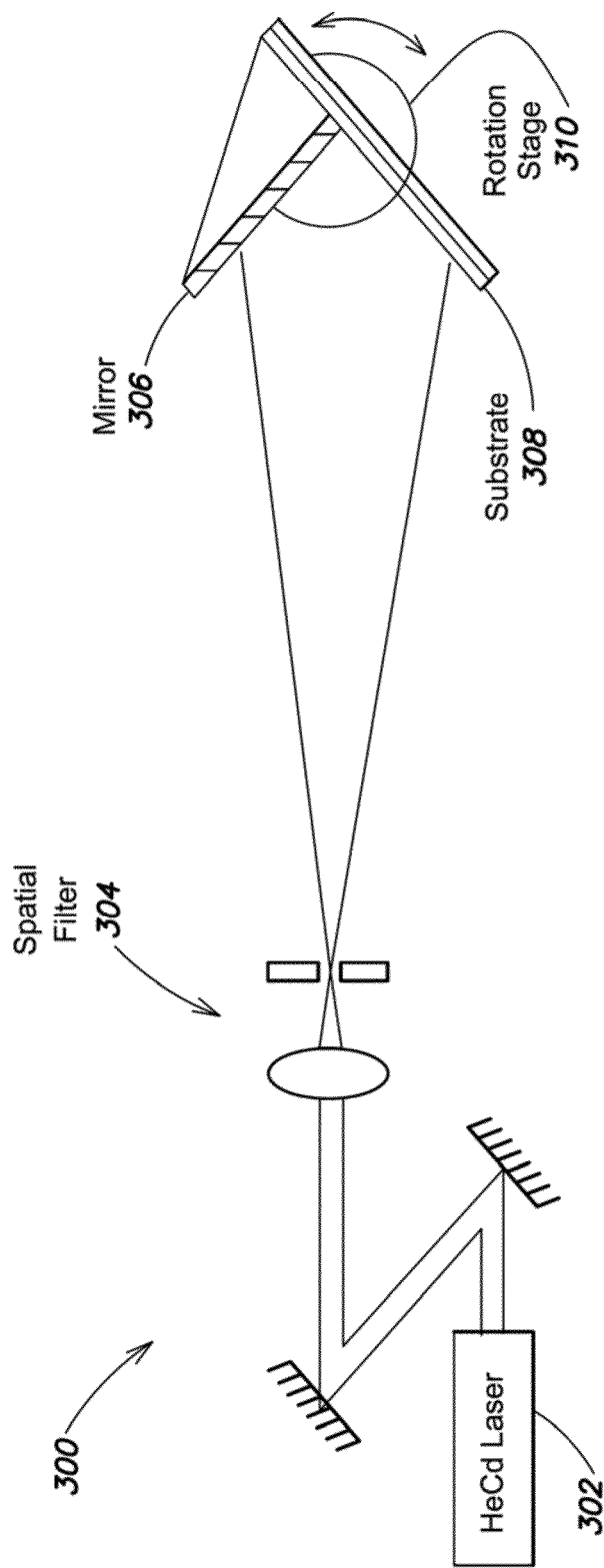
FIG. 3 shows an apparatus suitable for fabricating a photonic crystal with an energy band structure that exhibits a Fano resonance.

FIG. 3 depicts a system 300 for interference lithography, which is one technique for fabricating a photonic crystal with a uniform array of holes extending over a large area of a dielectric substrate 308. A coherent light source, such as a HeCd laser 302, emits a beam of radiation. A spatial filter 304 removes undesired spatial frequency components from this beam so as to create a beam with a Gaussian profile (or any other suitable profile). This Gaussian beam illuminates at least a portion of the substrate 308, which is mounted on a rotation stage 310. The Gaussian beam also illuminates a mirror 306, which is mounted on the rotation stage 310 at an angle with respect to the substrate 308. Light reflects off the mirror 306 towards the substrate's surface, where it interferes with the direct illumination to create a fringe pattern.

Figure 4A:
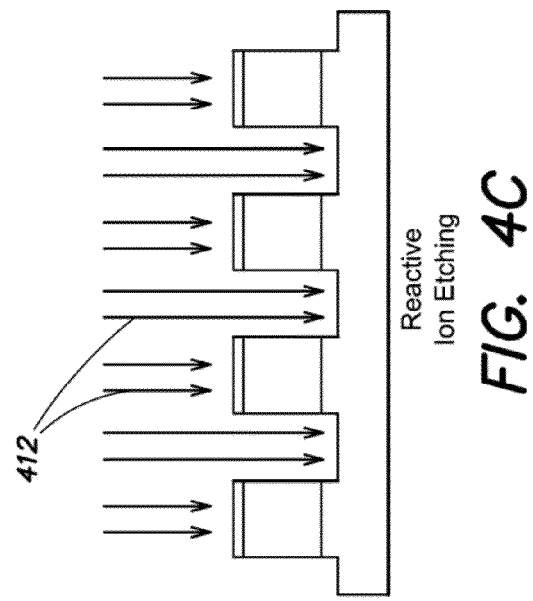
FIGS. 4A-4D illustrate a process of fabricating a photonic crystal with an energy band structure that exhibits a Fano resonance.
Figure 4B:
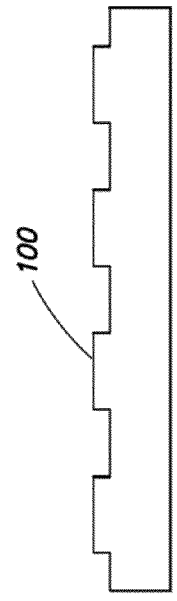
Figure 4C:
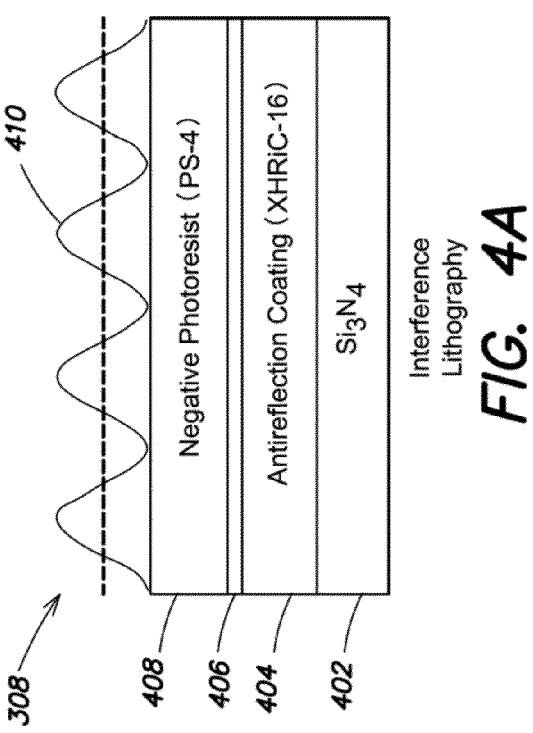
Figure 4D:
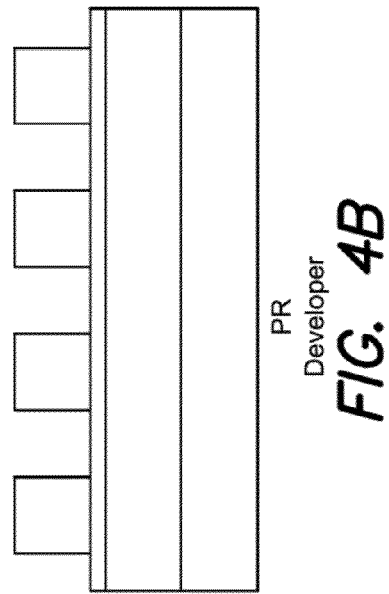

FIGS. 4A-4D illustrate a process for fabricating a photonic crystal using the interference lithography system 300 shown in FIG. 3. As shown in FIG. 4A, the interference lithography system 300 projects a fringe pattern 410 onto the surface of the substrate 308, which includes a negative photoresist, 408 (e.g., PS-4), an intermediate layer 406, and an anti-reflection coating 404 (e.g., XHRiC-16), all layered on a semiconductor slab 302 (e.g., $Si_3N_4$). Processing the photoresist 408 with developer, as shown in FIG. 4B, imparts a pattern corresponding to the fringe pattern 410 on the photoresist 408. This pattern exposes portions of the underlying layers, which are etched using reactive ion etching 412, as shown in FIG. 4C, to create a periodic array of holes in the semiconductor slab 402. Removing the photoresist 408, intermediate layer 406, and the anti-reflection coating 404 from the patterned semiconductor slab 402 yields a completed photonic crystal, as shown in FIG. 4D.

Figure 4E:
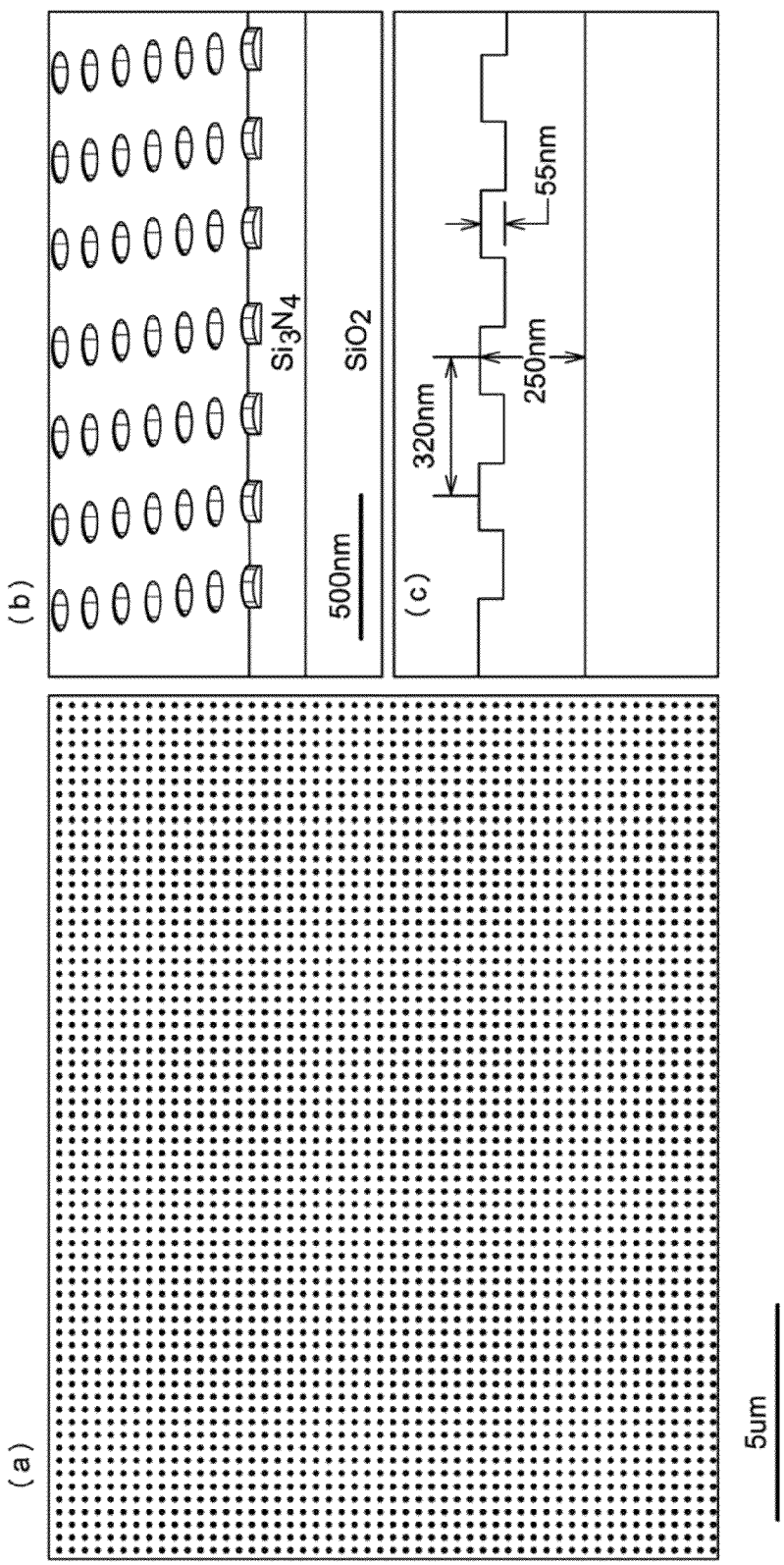
FIG. 4E shows scanning electron microscopes images of a photonic crystal fabricated according to the process shown in FIGS. 4A-4D.

FIG. 4E shows (a) top-view, (b) tilt-view, and (c) side-view scanning electron microscope images of a photonic crystal fabricated according to the process illustrated in FIGS. 4A-4D. The photonic crystal includes a 250 nm thick slab of $SbN_4$ with periodic cylindrical holes on top of 6 μm thick $SiO_2$ layer. The holes are spaced at an average period of 320 nm, with an average hole diameter of 160 nm and an average hole depth of 55 nm. Uniform periodic patterns were obtained on samples as large as 3 $cm^2$. These large areas of uniform (defect-free) periodicity support higher quality factors, which in turn lead to greater enhancement.

Simulated and Experimental Characterization of an Exemplary Photonic Crystal

Figure 5A:
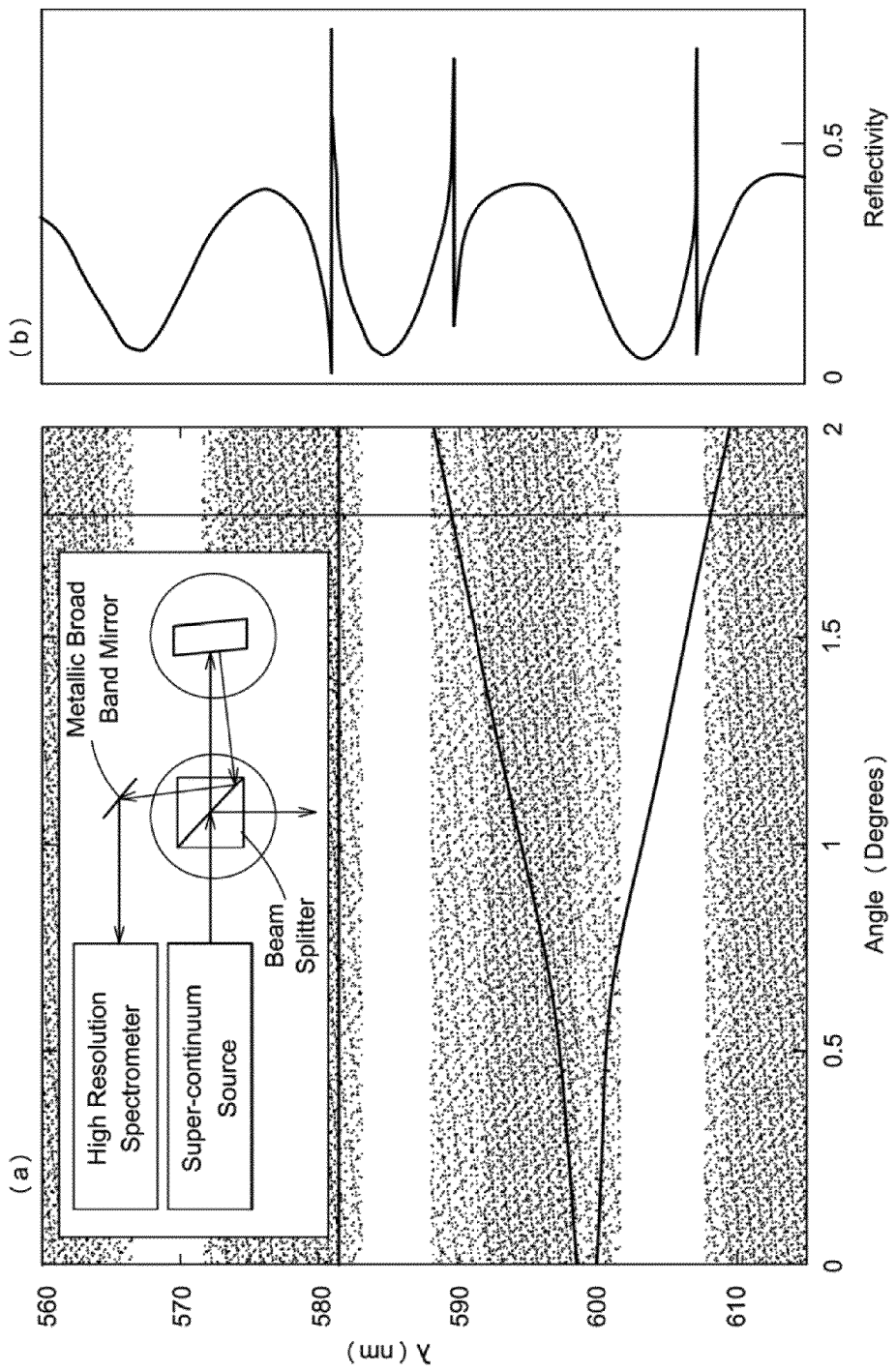
FIG. 5 shows band diagrams of the photonic crystal in FIG. 4 obtained from reflectivity measurements with (a, b) $E_y$ and (d, e) $E_x$ polarized beams and finite difference time domain (FDTD) simulations for (c) $E_y$ and (f) $E_x$ polarized beams.
Figure 5B:
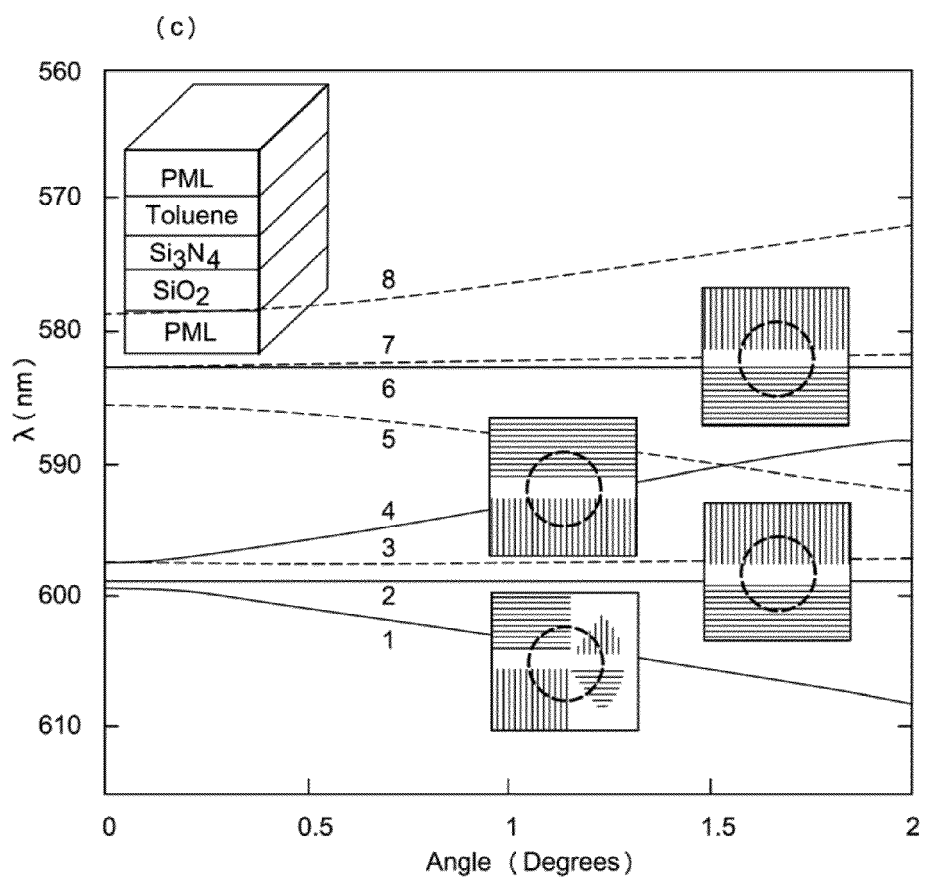
Figure 5C:
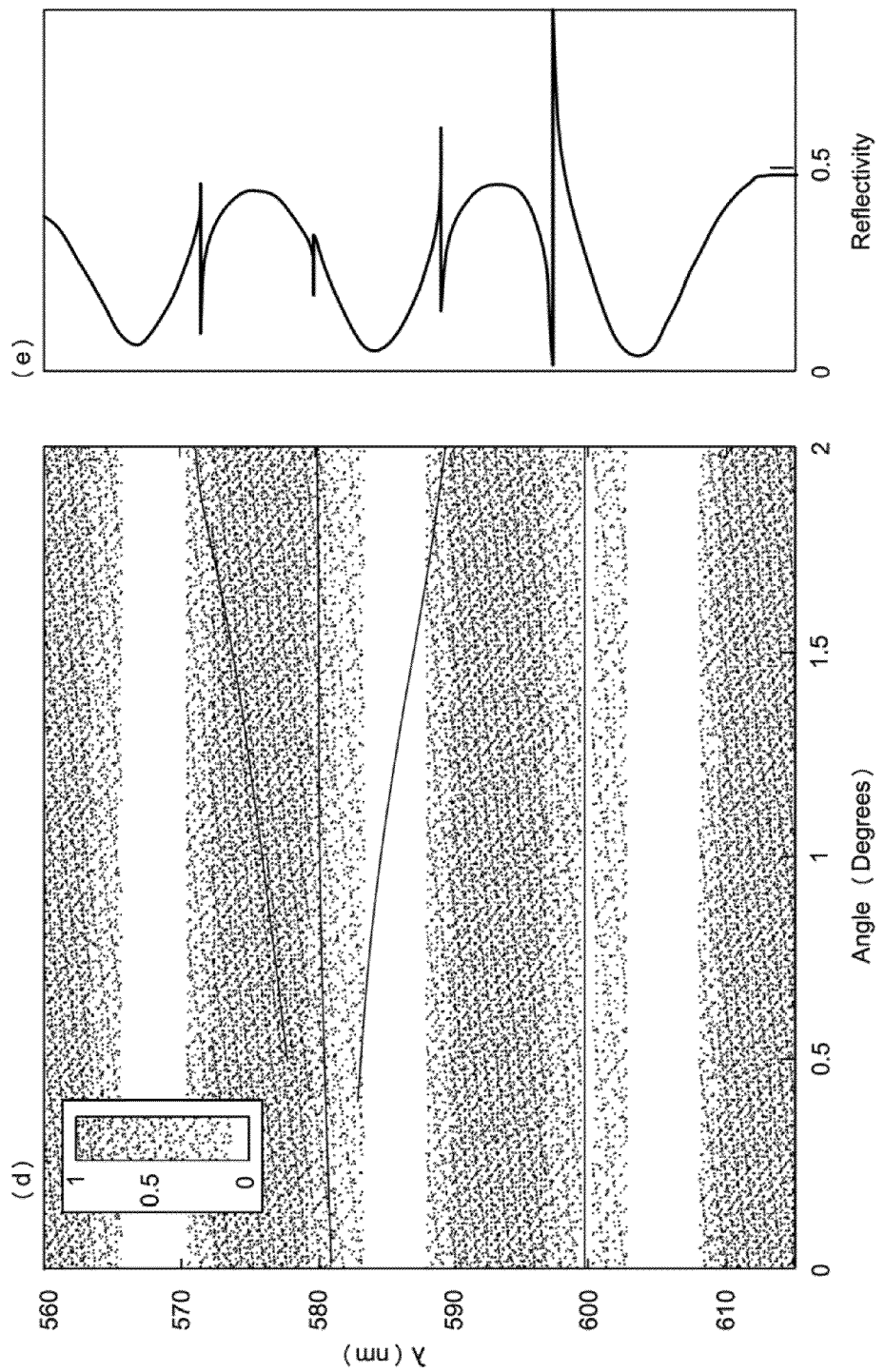
Figure 5D:
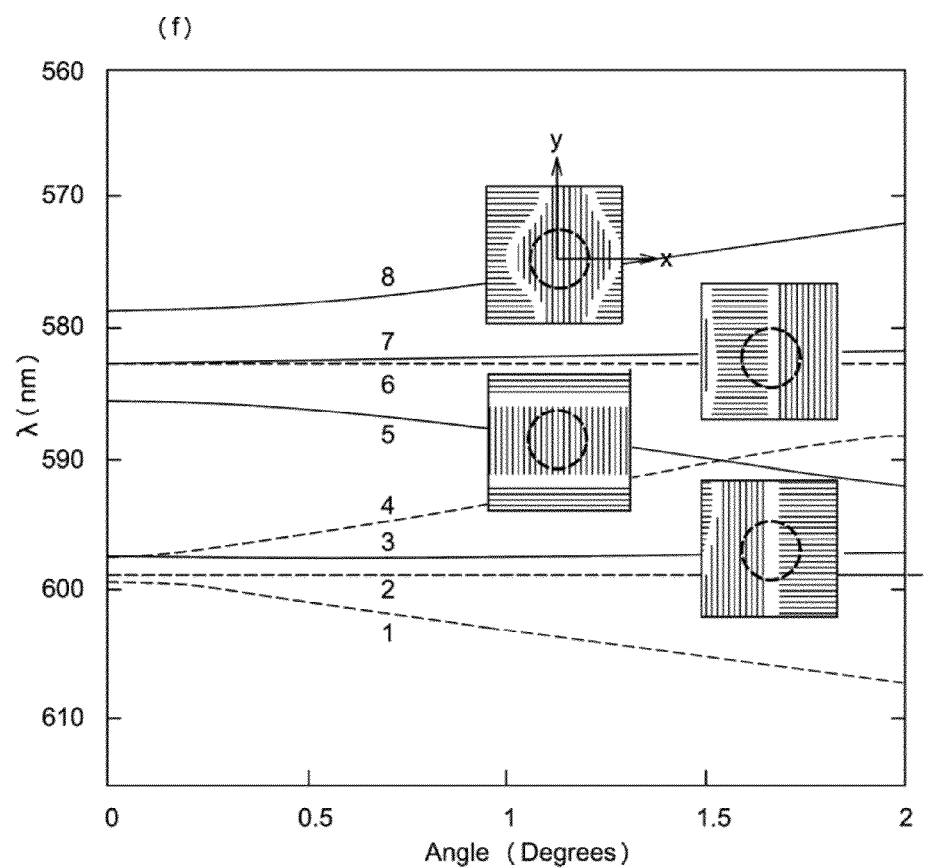

FIGS. 5(a)-5(f) show simulations and experimental measurements of the performance of the photonic crystal pictured in FIG. 4. FIGS. 5(a) and 5(d) show measured spectral reflectivities for orthogonal pump polarizations. These reflectivities were obtained by illuminating the photonic crystal slab with light from a supercontinuum laser source at small incident angles as measured from the normal to the photonic crystal plane towards the x-axis. The reflection spectra in FIGS. 5(a) and 5(d) reveal that the photonic crystal has eight energy bands.

The measured spectral reflectivities of FIGS. 5(a) and 5(d) show that the incident beam may excite any one of eight different modes of the photonic crystal depending on its polarization. (FIGS. 5(b) and 5(e) each show respective slices of these reflectivity spectra at an angle of 1.8°.) This polarization-dependent excitation can be understood from symmetry considerations: exciting the photonic crystal slab with a source of one type of symmetry results in coupling to the modes of the same type of symmetry only. Moving away from Γ to X causes the symmetry group to change from $C_{4v}$ to $C_{1h}$, reducing the number of irreducible representations from 5 to 2. Mirror reflection operation around the x-axis leaves the modes of one irreducible representation unchanged, while the modes of the other irreducible representation are altered by a factor of −1.

FIGS. 5(c) and 5(f) show the band diagram, at the Γ point, of the photonic crystal's eight lowest energy modes calculated by FDTD simulations. The four lower frequencies bands are TE-like (numbered 1-4) and the four higher frequencies are TM-like (numbered 5-8). The $E_z$ component of all eight modes are calculated at the center of the $Si_3N_4$ layer at k=[0.01, 0]·(2 pi/a). Except for TE-like mode number 2 in FIG. 5(a), the calculated resonant wavelengths are shifted by no more than ±0.5% from the measured spectra, which is well within the uncertainty of the measured periodicity or the value of the refractive index. The symmetry of each mode can be determined by examining the mode profile of its $E_z$ component. Modes 1, 2, 4, and 6 are altered by a factor −1 under mirror reflection operation around the x-axis and hence excited by $E_y$ polarized source, while modes 3, 5, 7, and 8 are unchanged under the same operation and hence excited by $E_x$ polarized source.

Figure 6:
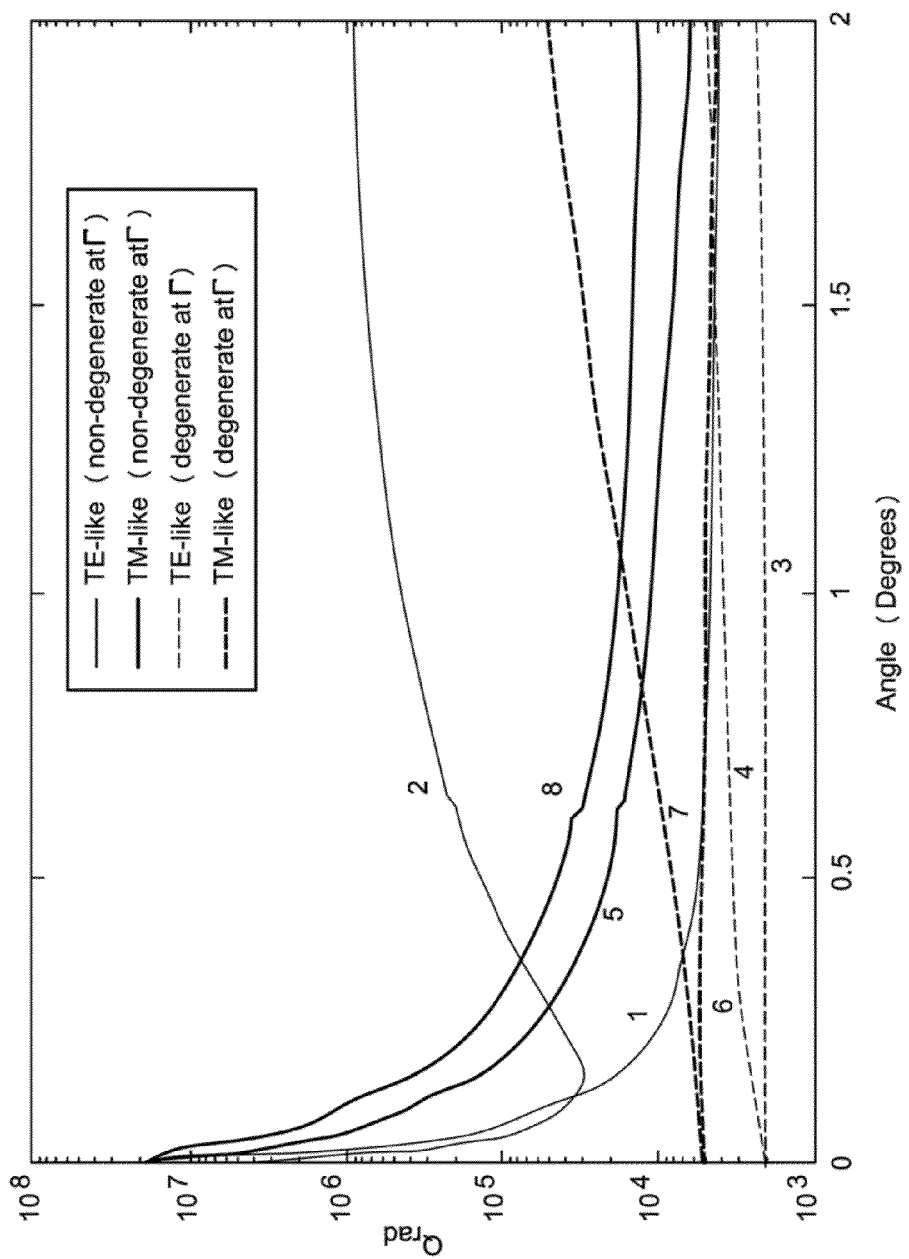
FIG. 6 is a plot of simulated radiative quality factor versus angle for high-Q singly-degenerate modes (solid lines) and doubly-degenerate modes (dotted lines).

FIG. 6 depicts the calculated $Q^{total}_{rad}$ of the eight bands shown in FIG. 5. It shows that while the doubly-degenerate (at Γ) bands 3, 4, 6, and 7 have finite $Q^{total}_{rad}$ at k≈0, the singly-degenerate (at Γ) bands 1, 2, 5, and 8 have $Q^{total}_{rad}$ that go to infinity when approaching k=0. This can be qualitatively understood from symmetry arguments. As mentioned earlier, a mode at the Γ point belongs to one of five irreducible representations of the $C_{4v}$ point group. One of the irreducible representations is doubly degenerate and has the same symmetry as free space modes, while the rest are singly degenerate and are decoupled from free-space modes. As a result, $Q^{total}_{rad}$ of these four singly-degenerate modes at the Γ point should be infinite despite lying within the light cone, while the doubly-degenerate modes have finite $Q^{total}_{rad}$. Moving away from Γ to X, the point group becomes $C_{1h}$ and the doubly-degenerate modes split into two. The two irreducible representations of the $C_{1h}$ point group share symmetry with the free-space modes and therefore $Q^{total}_{rad}$ becomes finite for all resonances, as is evident from FIG. 6.

A semi-analytical temporal coupled-mode theory model that accounts for the presence of guided leaky resonances in the $Si_3N_4$ layer provides a deeper insight into the physics of the measured resonances. This model can excited with an incident source propagating from the top and impinging onto the $Si_3N_4$ layer resonant cavity makes it possible. Applying a first-order perturbation to Maxwell's equations and energy conservation considerations, and neglecting second-order effects, yields the following expression for the photonic crystal's reflectivity:

$$|r_{PhC}| = \left| r_d - \frac{\gamma_{tot} \cdot (\tau_{tot}\tau_d + \gamma_{SiO_2}t_d)}{i(\omega - \omega_0) + \gamma_{tot}^2/2 + \gamma_{SiO_2}^2/2 + 1/\tau_{loss}^{total}} \right| \quad (5)$$

$\tau_d$ and $t_d$ are the complex reflection and transmission coefficients of the sample without the square lattice of cylindrical air holes. $\gamma_{tot}$ and $\gamma_{SiO2}$ are the coupling strengths of the resonant mode to the top environment and the $SiO_2$ layer respectively, and can be related to the quality factors by $\gamma_{SiO2}^2=\omega_0/Q^{SiO2}_{rad}$ and $\gamma_{tot}^2=\omega_0/Q^{tot}_{rad}$. Equation (5) shows that there are two temporal pathways: $\tau_d$, which represents the direct transmission and reflection processes of the uniform stack, and $t_d$, which represents the guided resonances excited within the $Si_3N_4$ layers whose energy leaks into the far field. The superposition of the two physical processes contributes to the typical narrow Fano line shapes superimposed on a Fabry-Perot-like background as observed in the reflectivity spectra of FIGS. 5(b) and 5(e).

Figure 7:
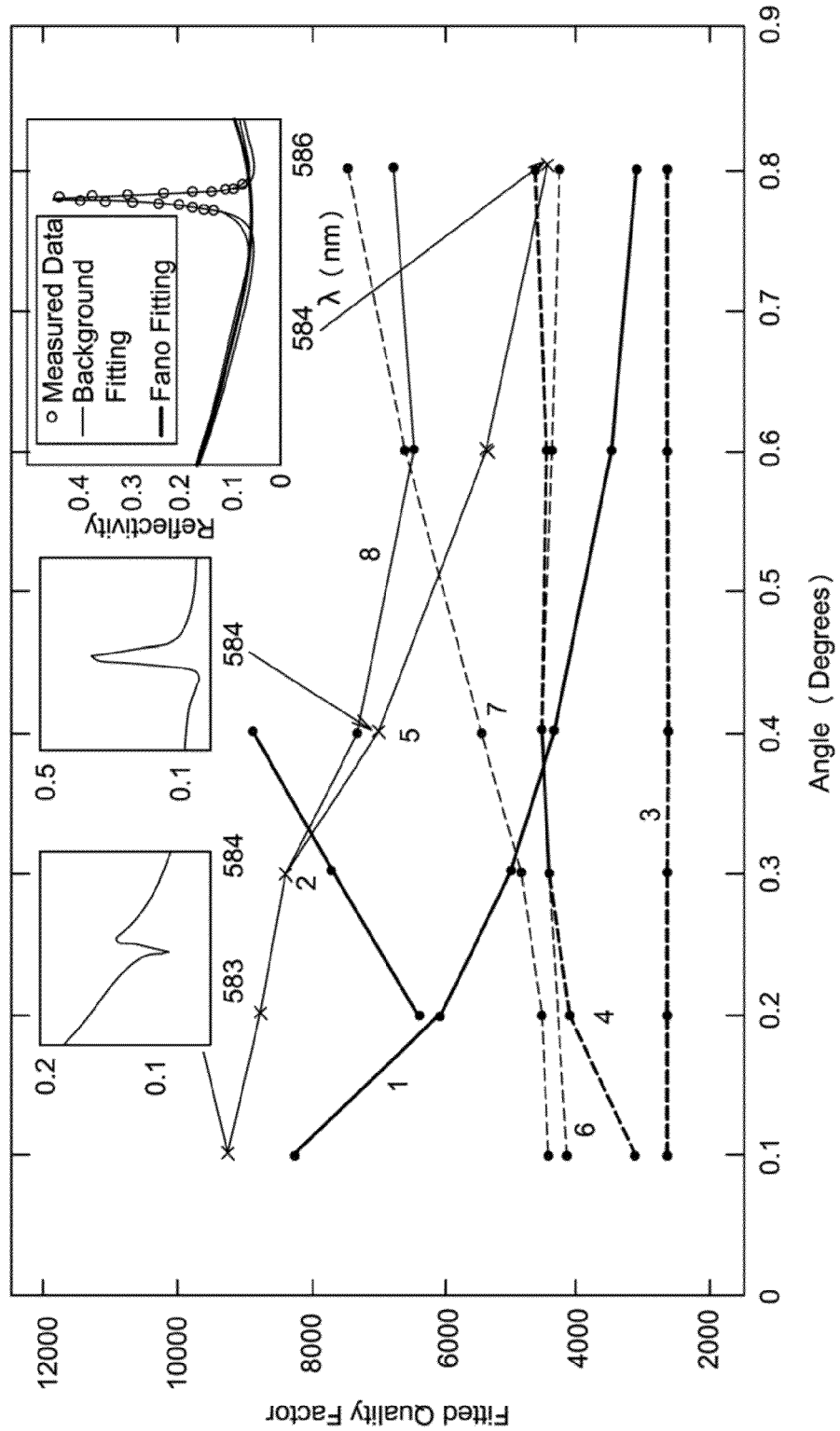
FIG. 7 is a plot of fitted quality factors versus angle for the measured data plotted in FIG. 5 (the left-hand insets show the reflectivity spectra of leaky mode 5 measured at 0.1°, 0.4°, and 0.8°; the right-hand inset depicts an example of the curve fitting process).

FIG. 7 is a plot of the total quality factor versus angle obtained by fitting Eq. (5) to the measured spectra, then using the result to find the total quality factor, $Q_{total}(1/Q^{total}_{rad}+1/Q^{total}_{loss})^{-1}$. The inset at right in FIG. 7 shows an example of a fitted Fano resonance curve for the data measured at 0.8° of band 5. The insets at left show the reflectivity spectra of leaky mode 5 at angles of 0.1°, 0.4°, and 0.8°. Note the distinct higher quality factors of the singly-degenerate modes close to zero angle (zero wave vector).

FIG. 7 reveals a distinction between the singly degenerate modes (modes 1, 2, 5, and 8) and the doubly degenerate modes (modes 3, 4, 6 and 7) at small angles. While the measured value of $Q_{total}$ increases when approaching k=0 for modes 1, 5, and 8, the doubly degenerate modes have decreasing or fixed values. Although $Q_{total}$ as high as $10^4$ are observed, the calculated $Q^{total}_{rad}$ (FIG. 6) of the singly-degenerate modes are much greater at small angles, suggesting that close to k=0 the resonant energy decay is dominated by absorption and incoherent scattering from fabrication imperfections ($Q^{total} \sim Q^{total}_{loss} \sim 10^4$), both of which could be significantly reduced by improving the fabrication process.

On the other hand, the four low-Q bands (modes 3, 4, 6, and 7) in FIG. 7 have $Q^{total}$ values that are comparable to the calculated $Q^{total}_{rad}$ and smaller than $Q^{total}_{loss}$. Indeed, FDTD calculations of the resonant mode show that the energy confinement is approximately unchanged within the plotted range of angles, suggesting that $Q^{scat}_{loss}$ is relatively constant over the range of angles considered here. Apart from limiting the values of $Q^{total}$ and hence the linewidth of the resonant lineshapes, the presence of relatively large scattering loss and absorption compared to far-field radiation near normal incidence leads to reduced resonant amplitudes. Conversely, the decrease of $Q^{total}_{rad}$ away from the normal provides a better match between $Q^{scat}_{rad}$ and $Q^{total}_{rad}$, which leads to an increase in the features' height. This is consistent with Eq. (5), and also explains why band 2 appears only weakly in the measurement results shown in FIG. 5(a). Unlike other high $Q^{total}_{rad}$ modes whose values decrease rapidly away from the Γ point, the $Q^{total}_{rad}$ of the missing TE-like band 2 remains high (FIG. 6) for most angles, resulting in small reflectivity amplitudes which are harder to detect.

Experimental realization of this mode offers several possible advantages: (1) the strongly enhanced field close to the photonic crystal surface and the simple access to it provides a new platform for the study of light and matter interaction; (2) it offers an easy-to-fabricate structure that supports delocalized modes with ultrahigh quality factors; (3) it allows a simple coupling of external radiation to strongly confined modes; and (4) despite the macroscopically large area resonator, only a few high-Q modes are supported within a fairly broad frequency range. The realization of this novel resonance could enable the enhancement and the demonstration of new physical phenomena in biological sensing, laser physics, energy conversion, nonlinear optics, and optical filters.

Experimental Demonstration of Enhanced Fluorescence Emission and Lasing

Figure 8:
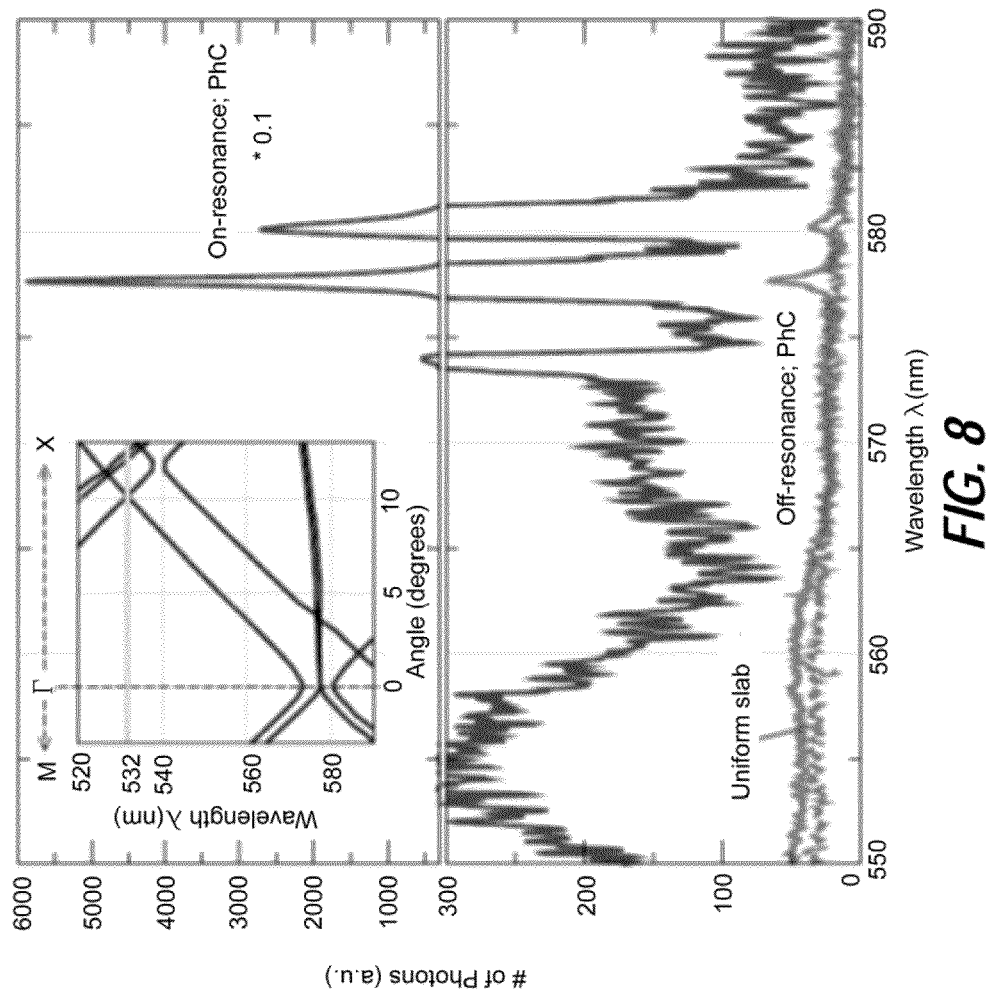
FIG. 8 is a plot of intensity versus wavelength for radiation emitted by a uniform collection of randomly polarized dipoles generated by excited organic molecules on the surface of an inventive photonic crystal (uniform slab) illuminated with on-resonant and off-resonant excitation radiation.
Figure 9:
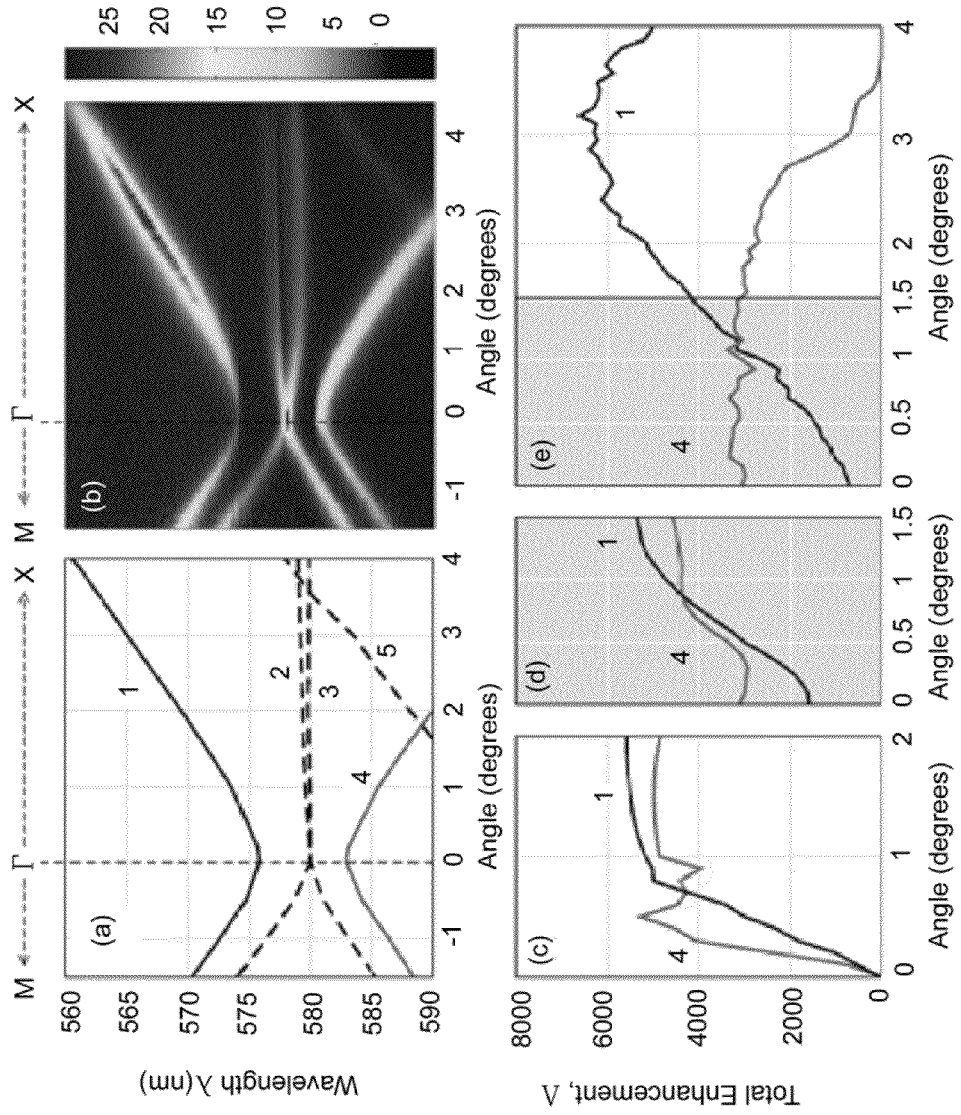
FIG. 9 illustrates simulated and experimental results of total emission enhancement from a Rhodamine 6G (R6G) solution on the surface of an inventive photonic crystal, including: (a) the photonic crystal's band structure along the Γ to M and Γ to X directions; (b) angle-resolved fluorescence measurements of the R6G solution; (c) predictions of the total enhancement factors vents angle for modes 1 and 4; (d) predicted average total enhancement factor versus angle from modes 1 and 4; and (e) total enhancement factor extracted from experimental results in (b).
Figure 10:
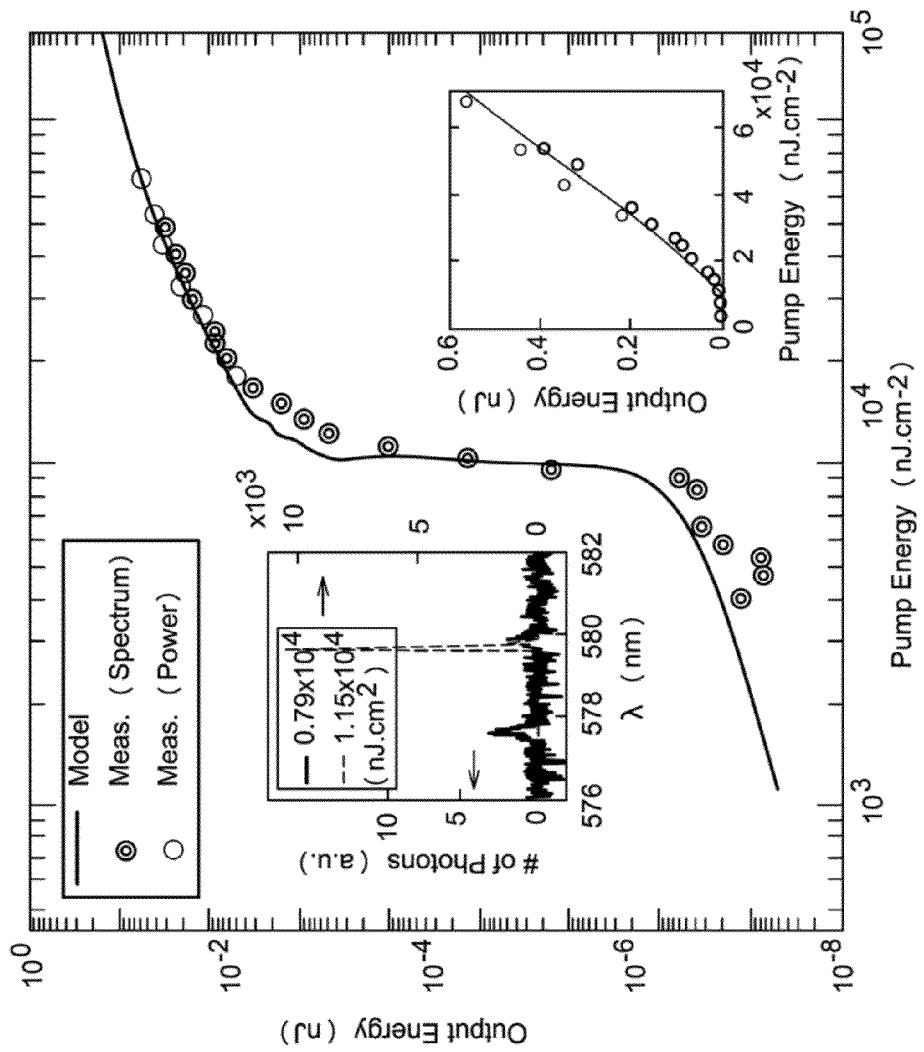
FIG. 10 is a plot of output energy measured with a spectrometer (open circles), output energy measured with a power meter (filled circles), and predicted output energy (line) versus pump energy for a laser made of a solution of organic molecules on the surface of a photonic crystal whose energy band structure exhibits.

FIGS. 8-10 show theoretical predictions and experimental measurements of the performance of an organic molecule laser. This laser includes an organic molecule (e.g., a Rhodamine 6G molecule) on the surface of a photonic crystal with a Fano resonance at or near the Γ point (e.g., the photonic crystal 100 shown in FIG. 1). A pump source—here, another laser—illuminates the organic molecule in a first direction, causing the organic molecule to fluoresce preferentially in a second direction as explained above. A spectrometer with a resolution of about 0.03 nm (e.g., an Ocean Optics HR4000) collects the fluorescence spectrum. Changing the spectrometer's position with respect to the organic molecule (e.g., using an XYZ translation stage) makes it possible to detect fluorescence emitted into different angles along the Γ-X and Γ-M directions.

FIG. 8 is a plot of the emission spectra from a blank photonic crystal slab, Rhodamine 6G molecules in solution on the photonic crystal slab illuminated by a non-resonant pump beam, and the same Rhodamine 6G solution illuminated by a resonant pump beam. The blank slab's emission spectrum is fairly flat and low. The non-resonantly pumped Rhodamine 6G molecule's emission spectrum has small peaks at about 577 nm and about 580 nm. And the resonantly pumped Rhodamine 6G molecule's emission spectrum has large peaks at about 574 nm, 577 nm, and 580 nm. In the on-resonance case, the excitation field within $d^{pump}_{eff}$ from the surface is strongly enhanced compared to the off-resonance case, while the remainder of the bulk layer exhibits no enhancement. In fact, FIG. 8 shows that resonant pumping enhances the Rhodamine 6G molecule's emission spectrum by a factor of at least about 80, which agrees well with the predicted enhancement.

The inset of FIG. 8 is a plot of the photonic crystal slab's band structure obtained from an FDTD. It shows that the incident angle for on-resonance coupling is about 10.0° for an excitation wavelength of 532 nm. Experiments show that the incident angle for on-resonance coupling is about 10.02° for this excitation wavelength, showing good agreement with the calculated results.

As explained above, the pump can be tuned on- and off-resonance by (1) changing the pump beam's incident angle, (2) changing the pump beam's wavelength, and (3) by changing both the incident angle and the wavelength. In these experiments, off-resonance pumping was achieved by changing the pump beam's incident angle. As a result, the difference in the enhancement for on- and off-resonance pumping is due to excitation enhancement since the extraction enhancement for the same wavelength at the same emission angle remains the same.

FIG. 9 includes plots of predicted and calculated enhancement data. FIG. 9(a) is a close-up of the plot of the photonic crystal's energy band structure along the Γ to M and Γ to X directions shown in the inset of FIG. 8. It shows the five energy bands in the wavelength/angular region of interest. FIG. 9(b) is a plot of angle-resolved fluorescence measurements of the Rhodamine 6G solution suspended on top of the PhC. As expected, it mimics the photonic crystal's energy band structure. FIG. 9(b) shows that the fluorescence is maximized around the photonic crystal's resonances. This can be understood by considering the decay rate into frequency, which is maximized at $\omega=\omega_k$. FIG. 9(b) also shows the emission's strong angular dependence.

FIGS. 9(c), 9(d), and 9(e) are plots of the total enhancement versus angle for energy bands 1 and 4 in FIGS. 9(a) and 9(b). The data plotted in FIG. 9(c) is the product of excitation enhancement and extraction enhancement using the theoretical model discussed above. These data show that the total enhancement goes to zero for both bands at Γ since the bands' radiative quality factors are infinite at Γ. Away from Γ, the bands' radiative quality factors drop exponentially, leading to maximum total enhancement upon satisfaction of the Q-matching condition between the radiative and non-radiative quality factors. The radiative quality factor of mode 1 drops much more slowly than that of mode 4, which may explain why the total enhancement of mode 1 increases much more slowly than that of mode 4 near Γ.

FIG. 9(d) shows the predicted averaged total enhancement factor between 0° and 1.5°. This plot represents the predicted total enhancement is averaged over the range of wave vectors corresponding to the spectrometer aperture's acceptance angle. This angle is narrow in the x direction (the difference between resonances of allowed wave vectors within corresponding acceptance angle is small compared to resonance width), but wide (e.g., about 1°) in the y direction.

Limitations on quality factor measurements restrict the calculation range for the averaged total enhancement to about 0-1.5° along the Γ-X direction. FIG. 9(d) shows that bands 1 and 4 behave differently close to the Γ point: for mode 4, the Q-matching condition is satisfied close to Γ (around 0.5°) and the averaged total enhancement is almost constant near Γ; however, the Q-matching for mode 1 occurs far from Γ, resulting in a linear increase in the averaged total enhancement at small angles.

FIG. 9(e) shows the total enhancement factor extracted from experimental results in FIG. 9(b). While the experimentally determined total enhancement of band 4 remains almost constant near Γ and drops to 0 when the resonance falls out of the range of spectrometer, the experimentally determined total enhancement of band 1 increases with angle before reaching its maximum of $6.3 \times 10^3$ at 3°. These experimental observations agree fairly well with the theoretical predictions in FIG. 9(d), particularly if comparing the theoretical prediction of the maximum enhancement for band 1 to experiments. This agreement holds for both trends and values: e.g., for band 4 at Γ, the averaged total enhancement is about $3\times10^3$ compared to an experimentally determined value of $2.8\times10^3$.

FIG. 10 shows predictions and results of a lasing experiment carried out using the same 100 nm layer of Rhodamine 6G solution, photonic crystal, and spectrometer as in the fluorescence measurements. In the lasing experiment, however, the Rhodamine 6G was pumped with a pulsed second-harmonic beam from a Nd:YAG laser. The pump beam had a wavelength of 532 nm, a pulse duration of 5 ns, a pulse repetition rate of 10 Hz, and a beam diameter of 1 mm. Pumping the Rhodamine 6G solution lased in two modes: a first mode (mode 4 in FIG. 9) at about 580 nm lased first, followed by a second mode (mode 1 in FIG. 9) at about 575 nm, both well within the Rhodamine 6G's emission spectrum. The total quality factor of mode 4 was about $8.3\times10^3$.

The solid lines in the main plot and lower inset of FIG. 10 are analytic predictions of the laser's output energy versus the pump energy on logarithmic and linear scales, respectively. Red circles are energies measured using the spectrometer. Green circles are data measured with a power meter. The jump in output power indicates the onset of lasing. The lower inset shows that the output power grows linearly with the pump energy beyond threshold. The upper inset is the measured power spectrum of emission from the photonic crystal slab at normal incidence below and above the lasing threshold.

FIG. 10 shows that the theoretical predictions of both threshold and slope efficiency match reasonably well with the experimental results within experimental errors. In particular, the measured threshold energy is 9 µJ/cm$^3$ corresponding to the intensity of 1.8 kW/cm$^2$, which is very low. Without being bound by any particular theory, it appears that the threshold is reduced for at least three reasons (1) the high-Q factors of the special Fano resonances; (2) the substantially enhanced absorption of the pump within 100 nm thin layer enabled by the excitation enhancement; and (3) the enhancement of the spontaneous emission factor for the lasing mode due to the enhanced spectral density of states. In particular, the excitation enhancement of about 60 enables 12.7% absorption of the pump energy within only 100 nm thin layer of the dye solution. And the rate of spontaneous emission into the structure's lasing mode is higher than in free space, yielding a higher spontaneous emission factor.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A system for stimulating an emission from at least one emitter, the system comprising:
 a photonic crystal, characterized by an energy band structure exhibiting a Fano resonance, comprising a patterned dielectric substrate defining a surface to support the at least one emitter; and
 a radiation source, in optical communication with the photonic crystal and the at least one emitter, to irradiate the at least one emitter at a first angle with respect to the surface of the photonic crystal so as to stimulate the emission from the at least one emitter at a second angle with respect to the surface of the photonic crystal.

2. The system of claim 1, wherein the at least one emitter comprises at least one of an organic molecule, a quantum dot, an organic quantum dot, a quantum well, and an exciton-hole pair.

3. The system of claim 1, wherein the photonic crystal has a quality factor of about 10 to about $10^{10}$.

4. The system of claim 3, wherein the quality factor extends over about $10^2$ unit cells of the photonic crystal to about $10^{10}$ unit cells of the photonic crystal.

5. The system of claim 1, wherein the patterned dielectric substrate defines a plurality of cylindrical holes arrayed on a square lattice.

6. The system of claim 1, wherein the at least one emitter emits substantially all of the emission at the second angle with respect to the surface of the photonic crystal.

7. The system of claim 1, further comprising:
a detector, in optical communication with the at least one emitter, to sense the emission.

8. The system of claim 7, wherein the emission comprises a fluorescence signal and the detector is configured to detect the fluorescence signal.

9. The system of claim 7, wherein:
the at least one emitter comprises at least one organic molecule characterized by a Raman resonance frequency;
the Fano resonance is at a Fano resonance frequency substantially equal to the Raman resonance frequency;
the radiation source is configured to excite the at least one organic molecule with coherent radiation at the Fano resonance frequency so as to cause enhancement of the emission via resonant absorption of the coherent radiation by the photonic crystal.

10. The system of claim 9, wherein the detector comprises a spectrometer to measure a spectrum of the emission.

11. The system of claim 9, further comprising:
a channel to guide a solution containing the at least one organic molecule over a surface of the photonic crystal; and
a reservoir, in fluid communication with the channel, to store the solution containing the at least one organic molecule.

12. A method of stimulating an emission from at least one emitter, the method comprising:
(A) supporting the at least one emitter of a surface of a photonic crystal, characterized by an energy band structure exhibiting a Fano resonance, comprising a patterned dielectric substrate free of defects; and
(B) irradiating the at least one emitter at a first angle with respect to the surface of the photonic crystal so as to stimulate the emission from the at least one emitter at a second angle with respect to the surface of the photonic crystal.

13. The method of claim 12, wherein (A) further comprises:
flowing a solution containing the at least one emitter over the surface of the photonic crystal.

14. The method of claim 12, wherein (B) further comprises:
selecting the first angle so as to cause the at least one emitter to emit substantially all of the emission at the second angle with respect to the surface of the photonic crystal.

15. The method of claim 12, wherein (B) further comprises:
selecting a frequency at which to irradiate the at least one emitter based on (i) a Fano resonance frequency of the Fano resonance and (ii) a resonance frequency of the at least one emitter so as to resonantly enhance the emission via resonant absorption by the photonic crystal.

16. The method of claim 12, further comprising:
(C) detecting the emission.

17. The method of claim 16, wherein the emission comprises at least one of fluorescence, phosphorescence, and a Raman signal emitted by the at least one emitter and (C) comprises detecting the at least one of the fluorescence, the phosphorescence, and the Raman signal.

18. The method of claim 16, further comprising:
(D) determining at least one characteristic of the at least one emitter based in part on the emission detected in (C).

19. The method of claim 18, wherein (D) further comprises:
determining a spectrum of the emission; and
identifying the at least one emitter based at least in part on the spectrum.

* * * * *